United States Patent
Pelrine et al.

(10) Patent No.: US 6,809,462 B2
(45) Date of Patent: Oct. 26, 2004

(54) ELECTROACTIVE POLYMER SENSORS

(75) Inventors: Ronald E. Pelrine, Boulder, CO (US); Roy D. Kornbluh, Palo Alto, CA (US); Qibing Pei, Fremont, CA (US); Joseph Stephen Eckerle, Redwood City, CA (US)

(73) Assignee: SRI International, Menlo Park, CA (US)

( * ) Notice: Subject to any disclaimer, the term of this patent is extended or adjusted under 35 U.S.C. 154(b) by 135 days.

(21) Appl. No.: 10/007,705

(22) Filed: Dec. 6, 2001

(65) Prior Publication Data

US 2002/0130673 A1 Sep. 19, 2002

Related U.S. Application Data

(63) Continuation-in-part of application No. 09/828,496, filed on Apr. 4, 2001.
(60) Provisional application No. 60/293,004, filed on May 22, 2001, and provisional application No. 60/194,817, filed on Apr. 5, 2000.

(51) Int. Cl.$^7$ ............................................... H02N 2/00
(52) U.S. Cl. ................................................... 310/800
(58) Field of Search ............................ 310/316.03, 319, 310/328, 338, 339, 800

(56) References Cited

U.S. PATENT DOCUMENTS

| | | | | |
|---|---|---|---|---|
| 3,903,733 A | * | 9/1975 | Murayama et al. | 73/574 |
| 3,935,485 A | * | 1/1976 | Yoshida et al. | 310/339 |
| 3,940,637 A | * | 2/1976 | Ohigashi et al. | 310/339 |
| 4,257,594 A | * | 3/1981 | Conrey et al. | 473/463 |
| 4,400,634 A | | 8/1983 | Micheron | |
| 4,843,275 A | | 6/1989 | Radice | |
| 4,870,868 A | * | 10/1989 | Gastgeb et al. | 73/649 |
| 4,885,783 A | | 12/1989 | Whitehead et al. | |
| 5,361,240 A | | 11/1994 | Pearce | |
| 5,369,995 A | * | 12/1994 | Scheinbeim et al. | 73/335.02 |
| 5,488,872 A | * | 2/1996 | McCormick | 73/862.68 |
| 5,835,453 A | * | 11/1998 | Wynne et al. | 357/140 |
| 5,977,685 A | | 11/1999 | Kurita et al. | |
| 6,048,622 A | * | 4/2000 | Hagood et al. | 428/461 |
| 6,060,811 A | | 5/2000 | Fox et al. | |
| 6,140,746 A | * | 10/2000 | Miyashita et al. | 310/358 |
| 6,385,429 B1 | * | 5/2002 | Weber et al. | 399/319 |
| 6,424,079 B1 | * | 7/2002 | Carroll | 310/339 |
| 6,504,286 B1 | * | 1/2003 | Porat et al. | 310/324 |
| 6,637,276 B2 | * | 10/2003 | Adderton et al. | 73/862.41 |
| 6,640,402 B1 | * | 11/2003 | Vooren et al. | 29/25.35 |
| 2001/0038317 A1 | * | 11/2001 | Kasperkovitz | 331/25 |

FOREIGN PATENT DOCUMENTS

JP 2-162214 * 6/1990 .......... G01D/21/00

OTHER PUBLICATIONS

Roy D. Kornbluh, Robotic Systems, Ocean Engineering and Marine Systems, 2000 Program, Jan. 2001, Office of Naval Research Public Release, ONR–32100–1.

Roy D. Kornbluh, Robotic Systems, Ocean Engineering and Marine Systems, 1999 Program, Feb. 2000, Office of Naval Research Public Release, ONR 32100–2.

(List continued on next page.)

Primary Examiner—Thomas M. Dougherty
(74) Attorney, Agent, or Firm—Beyer, Weaver & Thomas LLP

(57) ABSTRACT

The invention provides sensors that comprise a transducer that converts between mechanical energy and electrical energy. The transducer comprises an electroactive polymer in electrical communication with at least two electrodes. When a relatively small voltage difference is applied between the electrodes, deflection of the polymer results in a measurable change in electrical energy for the transducer. The change in electrical energy may correspond to a change in resistance, capacitance, or a combination thereof. Sensing electronics circuits in electrical communication with electrodes detect the electrical energy change.

117 Claims, 13 Drawing Sheets

OTHER PUBLICATIONS

Roy D. Kornbluh, Robotic Systems, Ocean Engineering and Marine Systems, 1998 Program, Feb. 1999 Office of Naval Research Public Release, ONR 32199–4.

Roy D. Kornbluh, Robotic Systems, Ocean Engineering and Marine Systems 1997 Program , Dec. 1997, Office of Naval Research Public Release, ONR 32198–2.

Ajluni, Cheryl, "Pressure Sensors Strive to Stay on Top, New Silicon Micromachining Techniques and Designs Promise Higher Performance", *Electronic Design–Advanced Technology Series*, Oct. 3, 1994, pp. 67–74.

Ashley, S., "Smart Skis and Other Adaptive Structures", *Mechanical Engineering*, Nov. 1995, pp. 77–81.

Bar–Cohen, Yoseph, JPL, *WorldWide ElectroActive Polymers, EAP (Artificial Muscles) Newsletter*, vol. 1, No. 1, Jun. 1999.

Cheng, Z.–Y., H. S. Xu, J. Su, Q. M. Zhjang, P.–C. Wang, and A. G. MacDiarmid, "High performance of all–polymer electrostrictive systems," Proceedings of the SPIE International Symposium on Smart Structures and Materials: Electro–Active Polymer Actuators and Devices, Mar. 1–2, 1999, Newport Beach, California, USA., pp. 140–148.

Kornbluh, R., Pelrine, R., Eckerl/e, J., Joseph, J., "Electrostrictive Polymer Artificial Muscle Actuators", IEEE International Conference on Robotics and Automation, Leuven, Belgium, 1998.

Ktech's PVDG Sensors, http://www.ktech.com/pvdf.htm, Jun. 6, 2001, pp. 1–5.

Pelrine, R., R. Kornbluh, and J. Joseph, FY 1998 *Final Report on Artificial Muscle for Small Robots*, ITAD–3482–FR–99–36, SRI International, Menlo Park, California, 1999.

Pelrine, R., R. Kornbluh, Q. Pei, and J. Joseph, "High Speed Electrically Actuated Elastomers with Over 100% Strain," *Science*, vol. 287, No. 5454, pp. 1–21, 2000.

Pelrine, R., R. Kornbluh, and G. Kofod, "High Strain Actuator Materials Based on Dielectric Elastomers," submitted to *Advanced Materials* (May 2000).

Pelrine, R., Roy Kornbluh, Jose Joseph, Qibing Pei, Seiki Chiba "Recent Progress in Artificial Muscle Micro Actuators,", SRI International, Tokyo, 1999 MITI/NEEDOIMNIC, 1999.

Treloar, L.R.G, "Mechanics of Rubber Elasticity," *J Polymer Science, Polymer Symposium*, No. 48, pp. 107–123, 1974.

Uchino, K. 1986. "Electrostrictive Actuators: Materials and Applications," *Ceramic Bulletin*, 65(4), pp. 647–652, 1986.

Zhenyi, M., J.I. Scheinbeim, J. W. Lee, and B.A. Newman. 1994. "High Field Electrostrictive Response of Polymers," *Journal of Polymer Sciences, Part B–Polymer Physics*, vol. 32, pp. 2721–2731, 1994.

http://www.ph.unimelb.edu.au "The Rubbery Ruler", printed from web Jul. 25, 2001.

Joseph, Jose, Ron Pelrine, Joe Eckerle, John Bashkin, and Prasanna Mulgaonkar, Micro Electrochemical Composite Sensor, SRI International, printed from web Jul. 25, 2001.

Pei, Qibing, Ron Pelrine, Roy Kornbluh, Sigridur Jonadottir, Venkat Shastri, Robert J. Full, "Multifunctional Electroelastomers: Electroactive Polymers Combining Structural, Actuating, and Sensing Functions" University of California at Berkeley, Berkeley, CA., available at www.sri.com–publications, Jan. 17, 2001.

http://www.neurosupplies.com/pdf_files/transducers.pdf, printed from web Jul. 25, 2001.

PowerLab ADInstruments, MLT001 High–Sensitivity Force Transducers, AD Instruments Transducers Series, printed from web Jul. 25, 2001.

Julian W. Gardner, "Microsensors: Principles and Applications," John Wiley, 1994.

Pei et al., "Improved Electroactive Polymers", U.S. patent application No. 09/619,847, filed Jul. 20, 2000, 70 pages.

Pelrine, R., R. Kornbluh, and Q. Pei. "Electroactive Polymer Transducers And Actuators", U.S. patent application No. 09/620,025, filed Jul. 20, 2001, 58 pages.

Pelrine, R. and Kornbluh, "Electroactive Polymer Devices", U.S. patent application No. 09/619,846, filed Jul. 20, 2000, 67 pages.

Pelrine, Ronald, Kornbluh, Roy D., and Joseph Stephen Eckerle, "Monolithic Electroactive Polymers", U.S. patent application No. 09/779,203, filed Feb. 7, 2001, 39 pages.

Pelrine, Ronald, Roy Kornbluh, Joseph S. Eckerle, Scott E. Stanford, Seajin Oh, and Pablo Garcia, "Biologically Powered Electroactive Polymer Generators", U.S. patent application No. 09/792,877, 76 pages.

Kornbluh, Roy D, R. Pelrine, P. Gallagher, J. Eckerle, D. Czyzyk, S. Shastri, Q. Pei, "Electroactive Polymer Animated Devices", U.S. application No. 09/828,496, 49 pages.

Pelrine, Ronald, R. Kornbluh, P. Garcia, and J. Eckerle, "Electroactive Polymer Generators", U.S. patent application No. 09/619,848, filed Jul. 20, 2000, 69 pages.

Kornbluh, Roy "Presentation to Colin Corporation", Jan. 1997.

Kornbluh, Roy, "Presentation to Medtronic", Jan. 2000.

Nikon Koliden Corporation, Operators Manual, available Oct. 1, 2001.

* cited by examiner

ELECTROACTIVE POLYMER SENSORS

CROSS-REFERENCE TO RELATED APPLICATION

This application claims priority under 35 U.S.C. §119(e) from co-pending U.S. Provisional Patent Application No. 60/293,004 filed May 22, 2001, which is incorporated by reference herein for all purposes; this application is also a continuation in part of co-pending U.S. patent application Ser. No. 09/828,496, filed Apr. 4, 2001 which claims priority from U.S. Provisional Application No. 60/194,817 filed Apr. 5, 2000, all of which are incorporated by reference herein for all purposes.

U.S. GOVERNMENT RIGHTS

This application was made in part with government support awarded by the Office of Naval Research under contract number N00014-00-C-0497. The government has certain rights in the invention.

BACKGROUND OF THE INVENTION

The present invention relates generally to sensor technology. More particularly, the present invention relates to sensors comprising one or more electroactive polymers that convert between electrical and mechanical energy; and their use in various sensing applications.

A sensor is a device that detects a change in—or determines the value of—a physical parameter. Conventional sensors may be classified based upon the parameter they sense. Common commercially available sensors include temperature sensors, pressure sensors, flow sensors, stress/strain sensors, accelerometers, dielectric sensors, conductivity sensors, shock sensors, and vibration sensors.

Conventional sensors may also be classified based upon the transduction mechanisms they employ. For example, a strain gauge measures changes in temperature, pressure, and/or deflection of an object via changes in physical dimensions, or strain, of the strain gauge. There exist many different strain gauge transduction mechanisms. Some simple strain gauges are based on materials capable of generating a voltage when subjected to small deflections. For example, piezoelectric-based strain gauges convert mechanical deflection to an electrical signal for strains in the range of 1 to 2 percent. This minimal deflection range severely limits piezoelectric-based strain gauge usage.

Devices capable of measuring larger strains or displacements are usually much more mechanically complex. Linear potentiometers may detect strain in the range of 1–6 inches or more, but are limited to linear deflections and are bulky, expensive rigid and often have low accuracy; thus restricting usage. Mercury filled elastic tubes are another conventional large strain sensor that is not limited to linear deflection and whose resistance changes as cross-section is reduced during stretching. These devices suffer from cost issues, and the mercury introduces undesirable safety concerns. Another conventional large strain sensor includes a rubberized air bellows of fixed diameter that is attached to a pressure transducer. Additionally, there are complex strain gauges based on changes in inductance of an insulated wire coil and strain gauges based on changes in capacitance of a bifilar helix of insulated wire coils. The complexity and size of these large strain sensor devices often restrict usage in many applications, e.g., when the required device size is small or when the environment does not permit complex mechanical designs.

In view of the foregoing, an alternative form of sensor for detecting a parameter would be desirable.

SUMMARY OF THE INVENTION

The present invention relates to sensors and sensor systems that comprise one or more electroactive polymer transducers. Each transducer comprises at least two electrodes in electrical communication with an electroactive polymer. The transducer is configured such that a portion of the electroactive polymer deflects in response to the change in a parameter being sensed. The electrical energy state and deflection state of the transducer are related. The change in electrical energy or a change in the electrical impedance of the transducer resulting from the deflection may then be detected by sensing electronics in electrical communication with the transducer electrodes.

In one aspect, the present invention relates to a sensor for detecting a change in a parameter. The sensor comprises a transducer including at least two electrodes in electrical communication with an electroactive polymer. The transducer is configured such that a portion of the electroactive polymer deflects in response to the change in the parameter and the deflection produces an electrical change in the transducer. The sensor also comprises sensing electronics in electrical communication with the at least two electrodes and designed or configured to detect the electrical change.

In another aspect, the present invention relates to a method of using an electroactive polymer transducer which comprises at least two electrodes in electrical communication with an electroactive polymer. The method comprises applying a voltage difference between the at least two electrodes. The method also comprises deflecting the electroactive polymer from a first position to a second position. The method additionally comprises detecting an electrical change in the transducer resulting from the deflection from the first position to the second position.

In yet another aspect, the present invention relates to a sensor for detecting a change in a parameter. The sensor comprises a transducer including at least two electrodes in electrical communication with an electroactive polymer. The transducer is configured such that a portion of the electroactive polymer deflects in response to the change in the parameter and the deflection produces a capacitance change in the transducer. The sensor also comprises sensing electronics in electrical communication with the at least two electrodes and designed or configured to detect the capacitance change.

In still another aspect, the present invention relates to a sensor for detecting a change in a parameter. The sensor comprises a transducer including at least two electrodes in electrical communication with an electroactive polymer. The transducer is configured such that a portion of the electroactive polymer deflects in response to the change in the parameter and the deflection produces a resistance change in the transducer. The sensor also comprises sensing electronics in electrical communication with the at least two electrodes and designed or configured to detect the resistance change.

In still another aspect, the present invention relates to a sensor for detecting a change in a parameter. The sensor comprises a transducer including at least two electrodes in electrical communication with an electroactive polymer. The transducer configured such that a portion of the electroactive polymer deflects in response to the change in the parameter and the portion deflection produces a resistance change in the electroactive polymer. The sensor also comprises sensing electronics in electrical communication with the at least two electrodes and designed or configured to detect the resistance change.

In still another aspect, the present invention relates to a sensor for detecting a change in a parameter. The sensor comprises a transducer including at least two electrodes in electrical communication with an electroactive polymer. The transducer is configured such that a portion of the electroactive polymer deflects in response to the change in the parameter and the deflection produces a resistance change in one of the at least two electrodes. The sensor also comprises sensing electronics in electrical communication with the at least two electrodes and designed or configured to detect the resistance change.

In another aspect, the present invention relates to a sensor array for detecting a change in one or more parameters. The sensor array comprises at least one transducer. At least one transducer comprises at least two electrodes coupled to a first portion of at least one electroactive polymer. The at least one transducer is configured such that the first portion deflects in response to a first change in the one or more parameters and the first portion deflection produces a first electrical change in the at least one transducer. At least one transducer also comprises at least two electrodes coupled to a second portion of the at least one electroactive polymer. At least one transducer is also configured such that the second portion deflects in response to a second change in the one or more parameters and the second portion deflection produces a second electrical change in the at least one transducer. At least one transducer also comprises sensing electronics in electrical communication with the at least two electrodes coupled to the first portion and in electrical communication with the at least two electrodes coupled to the second portion. The sensing electronics are designed or configured to detect the first and second electrical change.

These and other features and advantages of the present invention will be described in the following description of the invention and associated figures.

DETAILED DESCRIPTION OF THE PREFERRED EMBODIMENTS

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

1. Overview

The present invention relates to sensors that comprise a transducer that produces an electrical change with mechanical deflection or mechanical strain. The transducer comprises an electroactive polymer coupled to at least two electrodes. Deflection of the polymer results in a measurable change in an electrical property of the transducer. The change in electrical property may correspond to a change in resistance, capacitance, or a combination thereof. Electronic circuits in electrical communication with electrodes detect the electrical property change.

Figure 1:
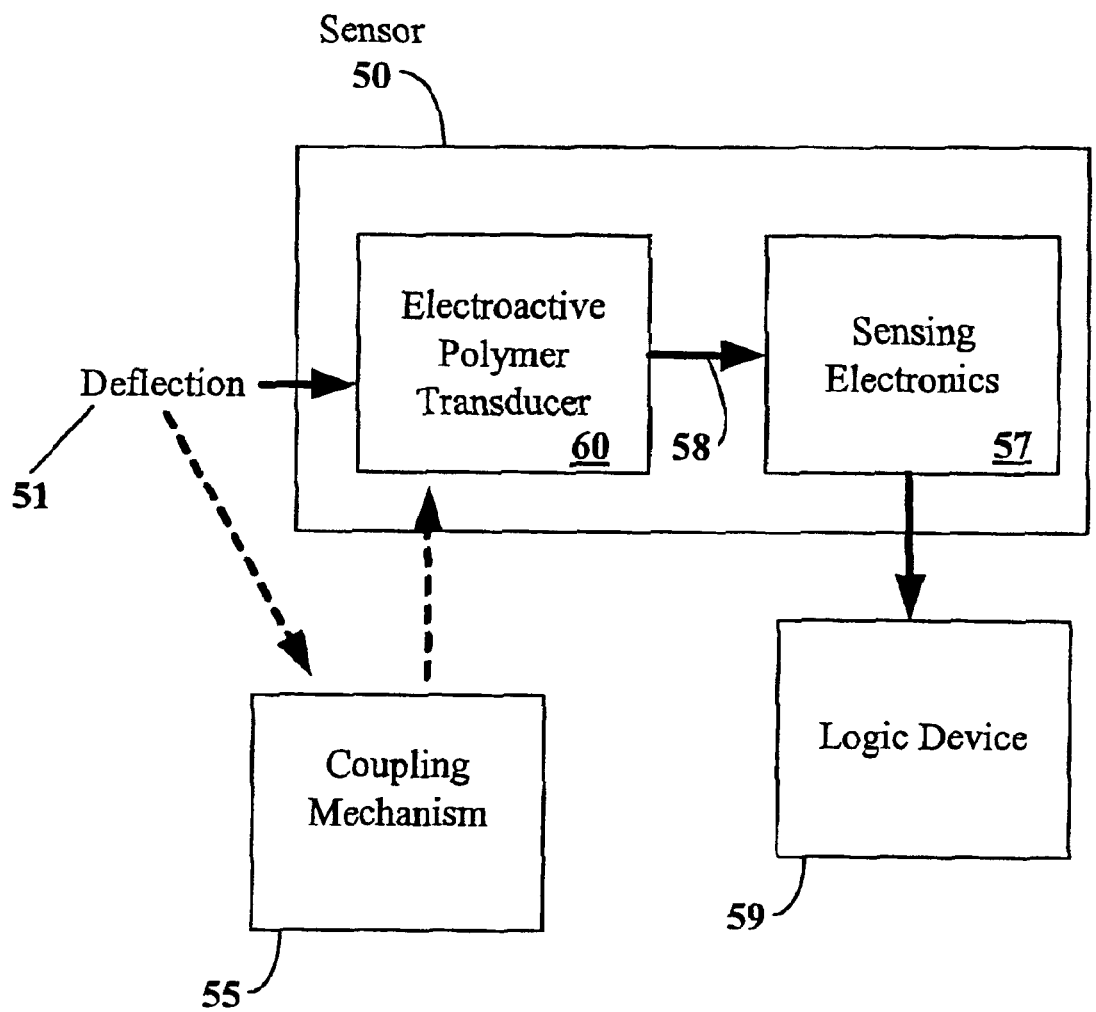
FIG. 1 is a block diagram of a sensing system in accordance with one embodiment of the present invention.

FIG. 1 is a block diagram of a sensing system in accordance with one embodiment of the present invention. A changing parameter or physical property being measured by sensor 50 deflects 51 an electroactive polymer included in sensor 50. Deflection 51 is detected as a change in an electrical property 58 for a transducer 60 employing the electroactive polymer (See FIGS. 2A–2B). If a change in capacitance or resistance of the transducer is being measured for example, one applies electrical energy to electrodes included in the transducer and observes a change in the electrical parameters.

In one embodiment, deflection 51 is input into sensor 50 in some manner via one or more coupling mechanism 55. Deflection 51 input into sensor 50 by coupling mechanism 55 results in deflection of the electroactive polymer. As will be described below, coupling mechanism 55 may either translate mechanical energy 51 into deflection of the electroactive polymer or convert electrical energy 51 into deflection of the polymer. In another embodiment, the changing property or parameter being measured by the sensor corresponds to a changing property of the electroactive polymer, e.g. displacement or size changes in the polymer, and no coupling mechanism 55 is used. Deflection of the electroactive polymer produces an electrical property change 58 in transducer 60. This change 58 may comprise a capacitance change of the polymer, a resistance change of the polymer, and/or resistance change of the electrodes. Sensing electronics 57 in electrical communication with the electrodes detect change 58 output by transducer 60 (See FIGS. 3A–3B). In some cases, a logic device 59 in electrical communication with sensing electronics 57 of sensor 50 quantifies the electrical change 58 to provide a digital or other measure of the changing parameter being sensed. For example, the logic device 59 may be a single chip computer or microprocessor that processes information produced by sensing electronics 57.

Typically, deflection 51 is produced by an object whose changing parameter is being measured. For instance, opposite ends of an electroactive polymer transducer of the present invention may be mechanically coupled to a linear actuator (e.g., a pneumatic piston) and detect displacement of the free end. The linear actuator then produces deflection 51. As another example, opposite ends of an electroactive polymer may be mechanically coupled to a thermally expanding object, e.g., a tank or vessel, to detect thermal expansion and contraction thereof. Thermal energy associated with the object then provides deflection 51. A single sensor 50 may contain a plurality of transducers 60 and a plurality of coupling mechanisms 55. For example, a sensor 50 implemented in a virtual reality glove or computer input device may include multiple transducers that detect linear strain of portions of the glove in the immediate area of each transducer. Each transducer may be coupled to the glove using glue, for example. Sensor 50 may also be used in an array of similar sensors as described below.

2. Electroactive Polymer Transducers

Figure 2A:
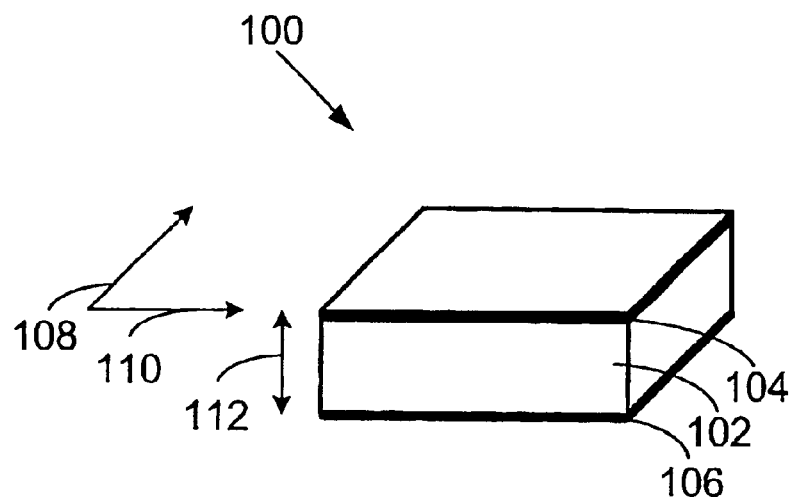
FIGS. 2A and 2B illustrate a top perspective view of a transducer before and after deflection in accordance with one embodiment of the present invention.

The transformation between mechanical and electrical energy for sensors of the present invention, or between mechanical energy (strain) and a change in an electrical property, is based on energy conversion or property changes of one or more active areas of an electro active polymer. Electro active polymers may convert mechanical to electrical energy, may convert electrical to mechanical energy, or may change electrical properties (for example, capacitance or resistance) as a result of a change in mechanical strain. To help illustrate the performance of an electroactive polymer in converting electrical energy to mechanical energy, FIG. 2A illustrates a top perspective view of a transducer portion 100 in accordance with one embodiment of the present invention. The transducer portion 100 comprises an electroactive polymer 102 for converting between electrical energy and mechanical energy. In one embodiment, an electroactive polymer refers to a polymer that acts as an insulating dielectric between two electrodes and may deflect upon application of a voltage difference between the two electrodes. Top and bottom electrodes 104 and 106 are attached to the electro active polymer 102 on its top and bottom surfaces, respectively, to provide or receive a voltage difference and electrical energy across a portion of the polymer 102.

Figure 2B:
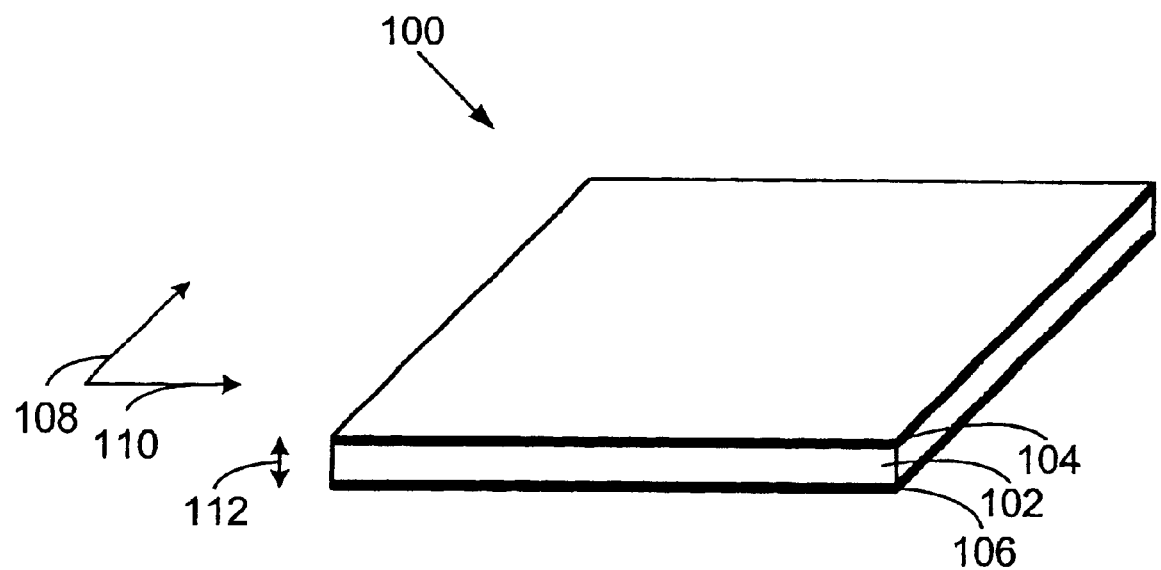

FIG. 2B illustrates a top perspective view of the transducer portion 100 including deflection to an expanded state relative to FIG. 2A. In general, deflection refers to any displacement, expansion, contraction, torsion, linear or area strain, or any other deformation of a portion of the polymer 102. Electrodes 104 and 106 are compliant and change shape with polymer 102. Electroactive polymers in accordance with the present invention are capable of deflection in any direction. In some cases, the electroactive polymer 102 is incompressible, e.g. has a substantially constant volume under stress. In these cases, the polymer 102 decreases in thickness as a result of the expansion in the planar directions 108 and 10. It should be noted that the present invention is not limited to incompressible polymers and deflection of the polymer 102 may not conform to such a simple relationship.

FIGS. 2A and 2B may be used to show how transducer portion 100 converts between mechanical energy and electrical energy during polymer deflection. When a relatively small voltage difference is applied between electrodes 104 and 106, deflection of transducer portion 100 will tend to change the voltage difference between the electrodes or to drive charge to or from the electrodes, or do both, depending on the electrical impedance of the interface circuit electrodes 104 and 106 are connected to. Electrical properties of transducer portion 100 will also change with deflection of polymer 102, such as the capacitance of transducer portion 100 and resistance of the polymer and electrodes. As polymer 102 changes in size, the changing electrical properties or changing voltage may be detected and used. For example, the change in voltage difference between the electrodes may be used to drive current to or from one of the electrodes. Sensing electronics in electrical communication with electrodes 104 and 106 may detect the current.

For example, if a voltage difference is applied to the polymer in a relatively thinner, larger area shape such as that shown in FIG. 2B, and the transducer portion 100 is then mechanically contracted in area between the electrodes to a shape such as in FIG. 2A, the deflection will tend to raise the voltage difference between electrodes 104 and 106. More specifically, when contracted, the transducer portion 100 becomes thicker and has a smaller planar area in the plane defined by directions 108 and 110 (orthogonal to the thickness between electrodes). When polymer 102 becomes thicker, it separates electrodes 104 and 106 and their corresponding unlike charges, thus raising the electrical energy and voltage of the charge. In addition, when electrodes 104 and 106 contract to a smaller area, like charges within each electrode compress, also raising the electrical energy and voltage of the charge. Thus, with different charges on electrodes 104 and 106, contraction from a shape such as that shown in FIG. 2B to one such as that shown in FIG. 2A raises the electrical energy of the charge, which may be detected and measured by a circuit in electrical communication with the electrodes 104 and 106. That is, mechanical deflection is producing an electrical energy change and the transducer portion 100 is acting as a mechanical deflection sensor.

The change in the electrodes' area as well as spacing between the electrodes changes the capacitance of the transducer. If the polymer 102 contracts, becoming thicker and forcing the electrodes 104 and 106 to contract, the capacitance of the transducer decreases. The change in capacitance can be measured electrically using well-known techniques, thus measuring the mechanical deflection. While not wanting to be bound by theory, there are well-known formulas that relate the capacitance to the electrode area, electrode separation and dielectric constant of the polymer.

Similarly, if a voltage difference is applied to the electrodes in a relatively thicker, smaller area shape such as that shown in FIG. 2A, and the transducer portion 100 is then mechanically expanded in area to a shape such as in FIG. 2B, the deflection will reduce the voltage difference initially between electrodes 104 and 106. The relatively small voltage difference applied between electrodes 104 and 106 is less than that necessary to actuate the polymer to the configuration in FIG. 2B from FIG. 2A (as will be described below). When expanded, the transducer portion 100 becomes thinner and reduces the separation between electrodes 104 and 106 and their corresponding unlike charges, thus lowering the electrical energy and voltage of the charge. Further, when electrodes 104 and 106 expand to a larger area, like charges within each electrode separate, also reducing the electrical energy and voltage of the charge. Thus, with different charges on electrodes 104 and 106, expansion from a shape such as that shown in FIG. 2A to one such as that shown in FIG. 23 reduces the electrical energy of the charge on the electrodes. Similarly, expansion of the electrodes 104 and 106, along with their moving closer together, raises the capacitance of the transducer 100. As described previously, the capacitance change can be measured using well-known techniques, thus providing an alternative method of sensing the deflection.

When used as a sensor, the shape change of electrodes 104 and 106 as the polymer deflects may result in a change in electrical impedance. The change in electrical impedance may correspond to a change in resistance of the electrodes, a change in resistance of the polymer, a change in capacitance of the transducer portion 100 (comprised of the polymer with electrodes), or a combination thereof. Correspondingly, sensors of the present invention provide several modes of sensing operation. Without wishing to be constrained by any particular theory, a number of theoretical relationships regarding the sensing performance of transducer 100 will now be described. These relationships are not meant in any manner to limit the manner in which the described sensors are operated.

In one aspect of the present invention, sensors of the present invention operate in a capacitance mode. More specifically, the capacitance of transducer 100 is related to the dimensions of polymer 102 and the sensor undergoes changes in capacitance of transducer 100 as the polymer deflects. By detecting and measuring changes in capacitance, corresponding polymer 102 deflection may be calculated.

Transducer portion 100 may be described electrically as a variable capacitor. As detected on electrodes 104 and 106, capacitance decreases for the shape change going from that shown in FIG. 2B to that shown in FIG. 2A. Generally speaking, a higher capacitance occurs when the polymer transducer 100 is stretched in area, and a lower capacitance occurs when the polymer transducer 100 is contracted or relaxed in area. The change in capacitance of the transducer may be approximated according to well-known formulas for calculating capacitance based on electrode area, electrode separation, and the dielectric constant of the polymer The change in capacitance can be measured electrically using well-known techniques, thus measuring the mechanical deflection.

A change in polymer 102 physical dimensions can be deduced from the change in capacitance. In a specific embodiment, capacitance C is simply approximated for transducer portion 100 by:

$$C = (\text{permittivity of free space}) \times (\text{relative polymer dielectric constant}) \times (\text{active area})/(\text{thickness})$$

where the active area (the area where electrodes 104 and 106 overlap on opposite sides of the polymer film 102) and the thickness describe the deflection state of the active area of polymer 102. The relative polymer dielectric refers to the dielectric material property of polymer 102. The change in polymer 102 physical dimensions determined above may then be converted to a change in displacement of an object coupled to polymer 102. The change in capacitance can be converted to a deflection using formulas which relate deflection and capacitance such as the one above. Alternatively, the relationship may be determined experimentally by measuring the capacitance for different deflections as part of the sensor calibration.

In another aspect, sensors of the present invention operate in a resistance mode. In this mode, deflection of the sensor induces changes in the cross-sectional area and/or surface area of the transducer that affect resistance of the transducer. In one embodiment, resistance changes may result from deflection induced changes in the resistance of conductive species in an electrode (e.g., carbon fibrils as described in further detail below) and the number of contacts and distance between such species. In another embodiment, resistance changes for a sensor of the present invention may result from deflection-induced changes in the total resistance of the polymer. In resistance mode, sensing electronics in electrical communication with the electrodes detect changes in electrical properties of the polymer-electrode structure resulting from one or more of these resistance changes as the polymer deflects. By detecting and measuring changes in resistance, corresponding changes in polymer 102 physical dimensions may be calculated; and further converted to a quantified change in an associated parameter such as deflection of an object that polymer 102 is mechanically coupled to.

In one embodiment, changing resistance across the polymer (e.g., from top to bottom electrode) is used to detect and measure deflection of transducer portion 100. More specifically, deflection of transducer portion 100 may be accomplished by detecting the change in resistance of polymer 102 as it contracts or expands. Typically, the resistance between electrodes 104 and 106 will be increased for contraction (from the position of FIG. 2B to that of FIG. 2A). This mode of sensing may also be referred to as detecting the 'leakage' across polymer 102. In a specific embodiment, the resistance, R, of polymer 102 is simply approximated for transducer portion 100 by:

$$R = \rho l / A$$

where $\rho$ is the resistivity of the polymer, l is the polymer thickness, and A is the planar area of the polymer film (the plane defined by directions 108 and 110). Thus, the area and thickness describe the deflection state of the polymer 102. Using sensing electronics as described below, a change in resistance, R, may be measured and converted to a change in polymer 102 physical dimensions. The change in polymer 102 physical dimensions may then be converted to a quantified change in an associated parameter such as displacement of an object coupled to polymer 102.

The computation of resistance, polymer deflection and object deflection may be performed by a logic device in electrical communication with the sensing electronics. In another embodiment, polymer resistance is not approximated based on the above equation but rather deflection of the polymer is determined using known resistance values for the polymer at different levels of deflection. For example, strain testing of a polymer may empirically provide a relationship between deflection and electrical resistance for a polymer before sensor implementation.

In another resistance-based sensor embodiment, deflection of the polymer is detected and determined using changing resistance values for an electrode at different levels of deflection. For example, known resistance values for carbon fibril based electrodes at different levels of strain may be combined with a measured resistance of the electrodes (provided by the sensing electronics) at a given time to determine the amount of deflection of transducer 100. Carbon fibrils may be used to make an electrode by, for example, first sonicating them in alcohol to disperse them, then spraying a thin coating onto the electroactive polymer to form the electrode. A small amount of elastomer binder can be used in the spray to enhance durability, or the fibril electrodes may be sprayed later with a soft elastomer overcoat for protection. The resistance values at different levels of deflection for the carbon fibril based electrodes may be determined empirically before sensor implementation, for example. By detecting changes in resistance in an electrode, corresponding changes in polymer 102 physical dimensions may be calculated; and further converted to a quantified change in associated parameter such as deflection of an object that polymer 102 is coupled to.

One or more of the above sensing modes may be combined such that sensing electronics detects and determines both resistance and capacitance changes and/or multiple modes of resistance change. This may be accomplished by electronically changing the measurement circuit in electrical communication with electrodes 104 and 106, or by simultaneously measuring capacitance and resistance, which is called measurement of the "complex impedance." Techniques for measuring electrical impedance of a dielectric material are well-known. Detecting both resistance and capacitance advantageously provides multiple measures of polymer 102 deflection, thus minimizing any dependency or unreliability associated with either individual sensing mode for a particular polymer.

The changes in capacitance, resistance, or both, may be measured using many well-known techniques. In one embodiment, changes in electrical energy and voltage can be measured by a suitable device or electronic circuit in electrical communication with electrodes 104 and 106. Having discussed several modes of sensing operation, suitable circuits and processes for detecting electrical changes in transducer 100 will now be described.

4. Sensing Using an Electroactive Polymer Transducer

A sensor of the present invention measures a change in a parameter of an object being sensed. Typically, the parameter change induces deflection in an electroactive polymer, which is converted to an electrical change output by electrodes attached to the polymer. As described below with respect to applications, many methods for applying mechanical or electrical energy to deflect the polymer are possible. Sensing devices may then be designed that use one or more of sensing modes described above. Typically, the sensing of electrical energy from a transducer of the present invention uses electronics of some type. For instance, a minimum amount of circuitry is needed to detect a change in the voltage across the electrodes.

Figure 3A:
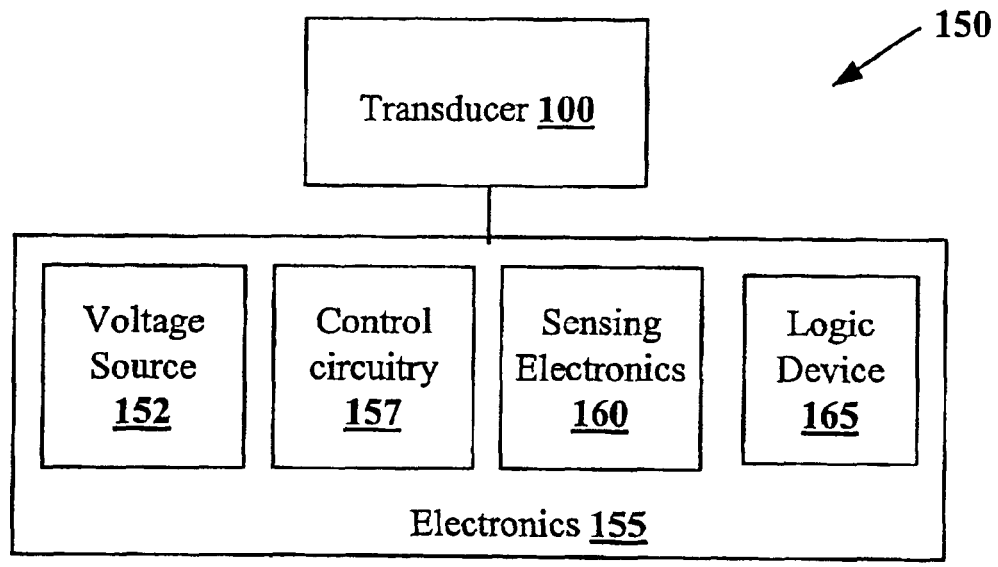
FIG. 3A is a schematic of a sensor employing an electroactive polymer transducer according to one embodiment of the present invention.
Figure 3B:
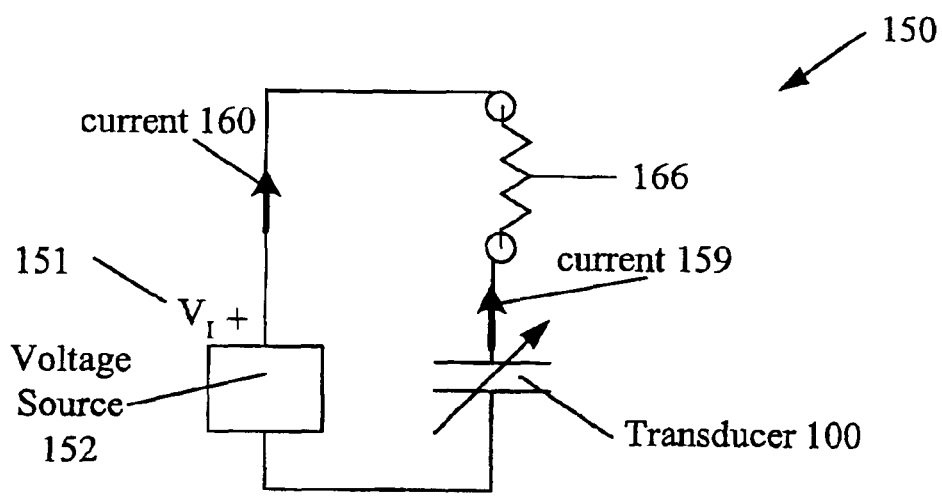
FIG. 3B illustrates a simple sensing circuit schematic in accordance with one embodiment of the present invention.

FIG. 3A is a schematic of a sensor 150 employing an electroactive polymer transducer 100 according to one embodiment of the present invention. FIG. 3B illustrates exemplary and simplified sensing circuit schematics for sensor 150. As shown in FIG. 3A, sensor 150 comprises transducer 100 and various electronics 155 in electrical communication with the electrodes of transducer 100. Electronics 155 are designed or configured to add, remove, and/or detect electrical energy from transducer 100. While many of the elements of electronics 155 are described as discrete units, it is understood that some of the circuit functions may be integrated. For instance, one integrated circuit may perform the functions of both the logic device 165 and the charge control circuitry 157.

In one embodiment, the transducer 100 is prepared for sensing by initially applying a voltage between its electrodes. In this case, a voltage 151, $V_I$, is provided by a voltage source 152. In some embodiments, a low-voltage battery may supply voltage 151, $V_1$, in the range of about 1–15 Volts. Generally, $V_I$ is less than the voltage required to actuate the electroactive polymer. Voltages in the range of about 10 mV to about 2000 volts, and more preferably in the range 1–100 V, are suitable as an initial voltage $V_I$. In any particular embodiment, choice of the voltage, $V_I$ may depend on a number of factors such as the polymer dielectric constant, the size of the polymer, the polymer thickness, environmental noise and electromagnetic interference, compatibility with electronic circuits that might use or process the sensor information, etc. The initial charge is placed on transducer 100 using electronics control sub-circuit 157. The electronics control sub-circuit 157 may typically include a logic device such as single chip computer or microcontroller to perform voltage and/or charge control functions on transducer 100. The electronics control sub-circuit 157 is then responsible for controlling voltage source 152 to initially apply the relatively low voltage on transducer 100.

Sensing electronics 160 are in electrical communication with the electrodes of transducer 100 and detect the change in electrical energy or characteristics of transducer 100. In addition to detection, sensing electronics 160 may include circuits configured to detect, measure, process, propagate, and/or record the change in electrical energy or characteristics of transducer 100. As described above, electroactive polymer transducers of the present invention may behave electrically in several ways in response to deflection of the electroactive polymer transducer. Correspondingly, numerous simple electrical measurement circuits and systems may be implemented within sensing electronics 160 to detect a change in electrical energy of transducer 100.

If transducer 100 operates in capacitance mode, then a simple capacitance bridge may be used to detect changes in transducer 100 capacitance. In another embodiment as shown in FIG. 3B, a high resistance resistor 166 is disposed in series with transducer 100 and the voltage drop across the high resistance resistor 166 is measured as the transducer 100 deflects. More specifically, changes in transducer 100 voltage induced by deflection of the electroactive polymer are used to drive current across the high resistance resistor 166. The polarity of the voltage change across resistor 166 then determines the direction of current flow and whether the polymer is expanding or contracting.

In this case, voltage source 152 can either source or sink current (such devices are known to one of skill in the art). Resistor 166 has a resistance, R, such at that the RC time constant of the circuit, where C is the minimum capacitance of transducer 100, is long compared to any time of interest. For example, if one measures changes that occur over 1 s time periods, the resistance of resistor R should be high enough such that RC is 20 to 100 s or more. Then the voltage drop across resistor 166 is a measure of the change in transducer capacitance, and hence deflection state of the transducer. The sensor system shown in FIG. 3B sensor is well suited to detecting relatively-rapid changes compared to the RC time constant of the circuit.

To understand the operation of sensor 150 as shown in FIG. 3B, operational parameters of sensor 150 at two times, $t_1$, and $t_2$ may be compared. At a first steady state time, $t_1$, the transducer 100 rests at a given deflection, possesses a capacitance, $C_1$, no current is flowing, and the voltage across the transducer 100 is voltage 151, $V_I$. At a second time $t_2$, later than time $t_1$, the transducer 100 is contracted in shape, e.g., from that shown in FIG. 2B to that shown in FIG. 2A. The deflection produces a capacitance $C_2$ which is lower than the capacitance $C_1$. The decrease in capacitance of transducer 100 between $t_1$, and $t_2$ increases the voltage across transducer 100 because R was chosen so that RC is long compared to the time of deflection. That is, the charge doesn't appreciably flow from the reduced capacitance $C_2$ within a short time (relative to RC). Since the capacitor's charge Q is therefore roughly constant, we see from the well-known equation Q=C V that if Q is constant and C decreases, then V must increase. The change in capacitance produces drive current 159, which is dissipated across a high resistance resistor 166. The resistor 166 functions as charge control circuitry 157 for sensor 150 of FIG. 3B. More complex charge control circuits may be developed depending on the configuration of electronics 155 and sensor 150. For example, if multiple transducers 100 are used in sensor 150, suitable charge control configurations may be applied. In this case, sensing electronics 160 detect the voltage change across the resistor 166 resulting from current 159. The resistor 166 may be chosen to have a sufficiently high resistance so that only a negligible amount of power is needed for detecting changes in transducer 100 voltage.

For an expansion of transducer 100 at time $t_3$, later than time $t_1$, the deflection produces a capacitance $C_3$ which is greater than the capacitance $C_1$. The increase in capacitance of the transducer 100 between $t_1$, and $t_3$ decreases the voltage across the transducer 100. The decreased voltage draws current 160 from voltage source 152 through resistor 166. The voltage change across the resistor 166 resulting from current 160 is measured using a voltage measuring device whose input impedance is much higher than the resistance of the resistor 166.

The resistance of resistor 166 may vary depending on the capacitance of the transducer 100 and rate of change of the parameter being measured. Typically, as the resistance of resistor 166 is increased, the speed of charge flow from, or to, the transducer 100 decreases. As the resistance of resistor 166 is increased, the RC time constant of the circuit increases and the temporal performance of the sensor (the sensor's ability to detect slow changes in the transduced parameter) increases. In general, higher resistances should be used for measuring lower frequencies. In particular, if f is the frequency of a deflection that must be measured, then the resistor 166 should have a value of resistance, R, such that RC is much greater than 1/f. Thus, the resistance of high resistance resistor 166 may be chosen based on the rate of change of the parameter being measured in an application. The resistance should not be chosen so high, however, that it takes too long (for the given application) for the transducer 100 to charge up to its nominal voltage of $V_f$. Alternately one could employ a special charging switch, known to one of skill in the art, that bypasses the resistor at start-up of the sensor. The resistance value should also be much less than the leakage resistance through the polymer (otherwise the transducer 100 will never charge up to a steady state voltage value of approximately $V_f$). The sensor described here is sometimes referred to as having only an AC response because it cannot accurately measure changes that occur over a time interval that is comparable to or long compared to RC.

So far, sensor embodiments described herein are appropriate mainly for an AC (time varying) response. Other embodiments may be used to measure DC and low frequency responses as well as high frequency responses. For example, the transducer 100 can simply be connected to a capacitance measuring circuits known in the prior art. In one such embodiment the voltage source 152 and resistor 166 are eliminated and only the transducer 100 from FIG. 3B is used together with a capacitance measuring circuit. The capacitance measuring circuit will typically output a voltage that is proportional to the transducer 100 capacitance, and the deflection can be calculated (or empirically determined) from the output voltage from the capacitance measuring circuit.

Capacitance measuring circuits typically apply a voltage or signal of a certain frequency to measure capacitance. If we denote this frequency by F, then electrodes having a resistance r such that RC<<(1/F) are suitable for many sensors, and a circuit is designed or configured such that 1F is short compared to the times of interest. A polymer may also be selected such that the leakage resistance (through the polymer) times the capacitance is long compared to (1F).

A DC (or very low frequency) response may also be achieved with the circuit in FIG. 3B using a resistance method rather than a capacitance method. With an appropriate choice of transducer leakage resistance and value for the resistor 166, the circuit can also be used to achieve a DC or low frequency response. If the value R of resistor 166 is chosen much smaller than the leakage resistance of transducer 100, and such that RC is much less than the duration of the shortest deflection time of interest, then the voltage across resistor 166 is a measure of the leakage resistance and hence the deflection state of transducer 100. In this case the capacitance change of transducer 100 will produce a "noise" signal on the desired signal across resistor 100, but the resulting noise signal will be short compared to the times of interest and could be easily filtered out if desired using filtering techniques known in the art of signal filtering.

Sensors of the present invention may also operate in other modes to achieve a DC response. In this case, performance of interface electronics 160 is independent of the rate of change of the parameter being measured. For example, a high frequency signal can be applied to the transducer 100. This method is similar to the use of capacitance measuring circuits noted above. The high frequency signal may be provided by voltage source 152 and control electronics 157 in electrical communication with the electrodes. The frequency of the high frequency signal is chosen to be higher than the fastest deflection frequency of interest, but typically having a period well below the RC time constant of the transducer 100, where in this case R refers to the resistance of the electrodes. The sensing electronics may then be configured to detect and measure changes in the high frequency response. Typically, the high frequency signal has a small voltage amplitude so that large amounts of power are not required and the polymer does not move in response to this voltage. Typically the voltage would be less than 10% of the values used for actuation or power generation. A typical range of peak to peak voltage is from 1 mV to 100V. This voltage can also be superimposed on top of an actuation or generation voltage for simultaneous or multifunctional operation, as described in further detail below.

Sensing electronics 160 may also quantify the electrical energy change in transducer 100, and convert this quantified electrical change into an estimated or sensed deflection of transducer 100 and the corresponding change in the parameter being detected. In one embodiment, a logic device 165 is included in electrical communication with sensing electronics 160. Logic device 165 is configured to quantify the change in electrical energy received by sensing electronics 160, e.g., by converting the change in electrical energy to an estimated or sensed deflection of transducer 100 according to a simple relationship provided above. Based on knowledge of the system being measured by sensor 150, logic device 165 may also quantify the change in parameter being sensed by sensor 150, e.g., by converting deflection of the polymer to a corresponding change in size of an object that the polymer is coupled to.

Logic device 165 may also be used to apply correction factors to the initially calculated deflection due to less than ideal conditions. For example, logic device may include separate temperature sensing elements to correct parameters for small temperature variations. Alternately, in the case where one cannot, or does not wish to (for example, due to cost factors), use optimal values for resistor resistance, electrode resistance, polymer capacitance, or leakage resistance, logic device 165 may apply correction factors to compensate for less than optimal values.

It should be noted that parts of a transducer not directly involved in sensing functionality may be adapted to improve sensor performance. For capacitance based sensors as described above for example, the electrodes are not directly involved in sensing but may contribute to sensor performance since they are part of the electrical sensing circuit. In this case, the electrodes preferably have a low resistance (relative to the leakage resistance of the polymer) in order to suitably move charge across the surface of the capacitor. In addition, the RC time constant for the transducer should not be too slow or the circuit may not detect the capacitance; so in some cases it may be desirable for R to be low enough so that 1/RC is much less than the frequency, f, used to measure capacitance.

This resistance can be measured by terminals or contacts across the polymer electrodes. For example, electrodes having a resistance in the range of about 1000 ohms to about 100 Megohms are well suited to suitably move charge across some of the polymer materials mentioned below. In another embodiment, the electrodes have a resistance approximately less than about 10% of the electroactive polymer leakage resistance. For sensors of the present invention that measure a change in polymer leakage resistance as it deflects, the electrodes are preferably much more conductive than the polymer. This allows electrode resistance to be negligible relative to changes in transducer resistance; and thus changes in transducer resistance are mainly attributable to the polymer. Since the polymer resistance varies with the specific polymer used, the required maximum electrode resistance will also vary with the specific polymer used.

For impedance sensors that detect a combination of resistance and capacitance from the transducer, the polymer and electrode electrical properties may vary with an application. Some applications may benefit from capacitance based sensors and thus parts of a transducer may be tailored as described above with respect to capacitance based sensors. Alternatively, some applications may benefit from resistance based sensors and thus parts of a transducer may be tailored as described above with respect to resistance based sensors.

In one embodiment, charge is removed from the electrodes during contraction. In this manner, the electric field pressure generated as a result of the changing electrical status of the transducer does not affect sensitivity of the sensor. Referring back to FIGS. 2A and 2B, the transducer portion 100 will convert mechanical energy to electrical energy as it deflects. Some or all of the charge and energy can be removed when the transducer portion 100 is fully contracted in the plane defined by directions 108 and 110. Alternatively, some or all of the charge and energy can be removed during contraction. If the electric field pressure in the polymer increases and reaches balance with the external mechanical deflection forces during contraction, the contraction will stop before full contraction, and no further elastic mechanical energy will be converted to electrical energy. Removing some of the charge and stored electrical energy reduces the electrical field pressure, thereby allowing contraction to continue. Thus, removing some of the charge as contraction proceeds may increase the range of motion of sensor deflection. The exact electrical behavior of the transducer portion 100 when operating as a mechanical sensor depends on any electrical and mechanical loading as well as the intrinsic properties of polymer 102 and electrodes 104 and 106. Generally however, one may operate sensors of the present invention well below this limit so as to avoid this issue entirely. However, if one is using the sensor in an application for simultaneously generating power and measuring deflection, then removing charge from the electrodes during contraction may be advantageous.

Although electrical communication so far has been described with respect to physical conducting wires that provide electrical communication between the transducer electrodes and the interface electronics, wireless techniques may also be used to provide electrical communication between the electrodes and interface electronics. For example, wireless communication via electromagnetic radiation of appropriate frequency is suitable to transmit electrical changes from the transducer. Thus, an antenna may be coupled to the polymer for electrical communication. Generally, the sensing electronics and transducer may be designed to allow any suitable carrier (not just RF or other electromagnetic radiation). The carrier may allow the transducer to be probed from a substantial distance and over a wide area. If real time feedback is being detected from the transducer, the carrier should also provide sufficient bandwidth to transfer the desired information in a timely manner. Additionally, the modulated carrier may also be sufficiently unique, in terms of frequency or time synchronization, or coding, such that it is distinguishable from the signal provided by nearby sensors in an array. Generally, the carrier may be a wave or field that acts over a distance through a medium (vacuum, gas, fluid, solid, etc.) between a transmitted/receiver and the sensor. Examples of suitable carriers include RF radiation, microwave radiation, visible, ultraviolet, and infrared radiation, acoustic waves, electric fields, magnetic fields, and the like. If the system employs RF radiation, the frequency preferably ranges between 100 kHz and 5800 MHz as specified by the IEEE are suitable. Microwave radiation provides another suitable carrier. Generally, it provides the same functionality as RF radiation, but at larger ranges.

Up to this point, various embodiments of the sensing electronics 57 that convert, for example, the capacitance of electroactive polymer transducer 60 to an analog voltage have been described. Referring again to FIG. 1, the analog voltage is typically converted to a digital signal by means of an analog-to-digital converter (ADC) within logic device 59. In one embodiment, interface electronics 57 convert the transducer capacitance to a signal with a frequency that is directly related to the capacitance. This frequency signal may be more easily (compared to using an ADC) converted to a digital signal for further processing by logic device 59.

Figure 3C:
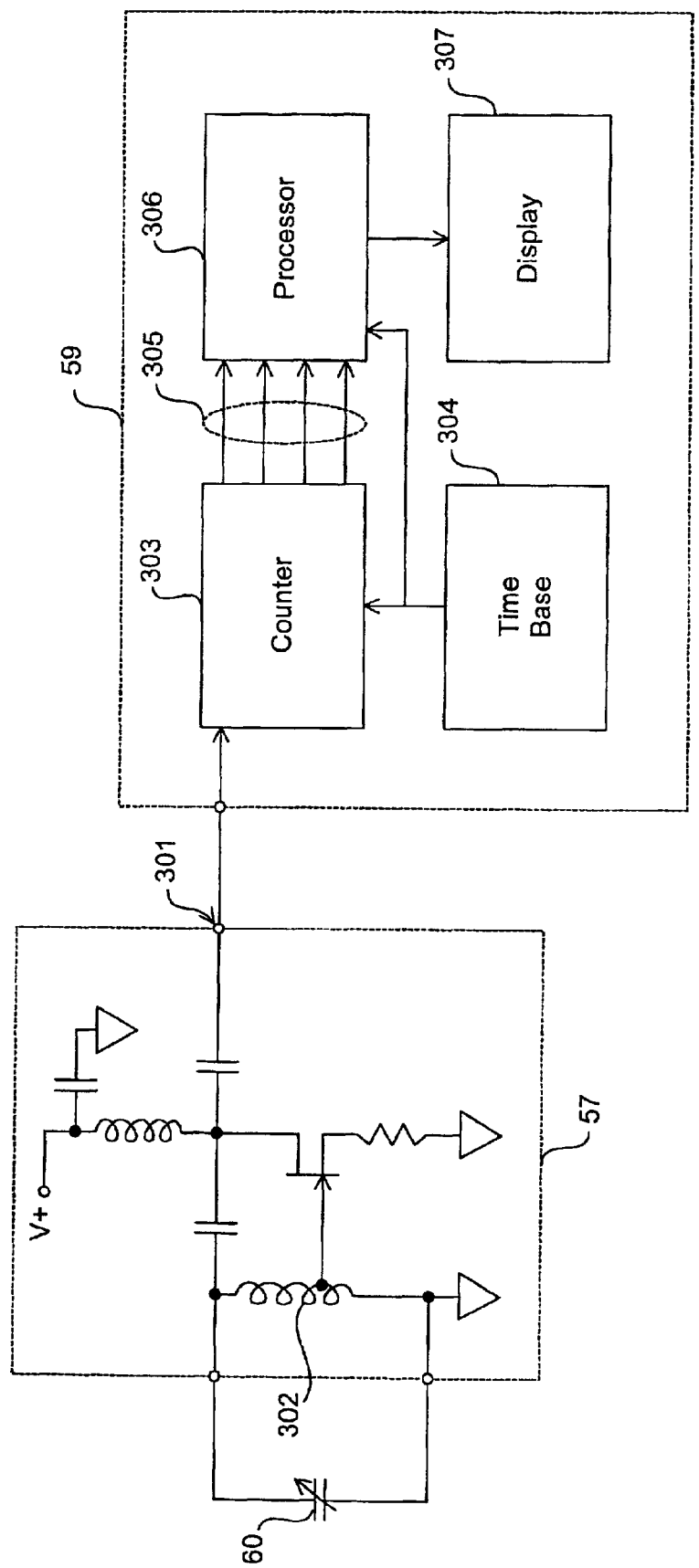
FIG. 3C illustrates a sensing circuit schematic in accordance with another embodiment of the present invention.

Referring to FIG. 3C, transducer 60 is represented by a variable capacitance. Sensing electronics 57 consist of the circuitry within the dashed line. Those skilled in the art will recognize that the circuitry 57, together with the capacitor 60 constitute a Hartley oscillator circuit. This well-known circuit configuration generates an output signal on terminal 101. The frequency, f, of the output signal is given by the equation, $$f = \frac{1}{2\prod\sqrt{LC}},$$

where L is the inductance of inductor 102 and C is the capacitance of the polymer transducer 60.

Still referring to FIG. 3C, the output signal 301 is the input to a counter circuit 303. The counter circuit is also driven by a time base 304. In one embodiment, time base 304 is a crystal oscillator circuit. The output 305 of counter circuit 303 may be a parallel signal (i.e.: a number of lines representing each bit of the count). This signal serves as the input to a processor 306. Processor 306, which may include a microprocessor, uses the frequency equation above (or a suitable similar equation) to compute transducer 60 capacitance based on the counter 303 output signal. Then, using a suitable equation or a "look up" table, processor 306 computes the value of the measured parameter. This value is output to display 307.

As indicated by the second dashed line in FIG. 3C, counter 303 time base 304, processor 306, and display 307 together constitute the logic device 59 of FIG. 1. The use of these subsystems was chosen partly to help illustrate the functions required to convert the frequency of signal 301 to the volue of the measured parameter. Those skilled in the art of microprocessors may devise techniques so that the counting function is performed by the processor. In such a case, counter circuit 303 may be eliminated, and the signal 301 may directly drive an input of processor 306.

Figure 4:
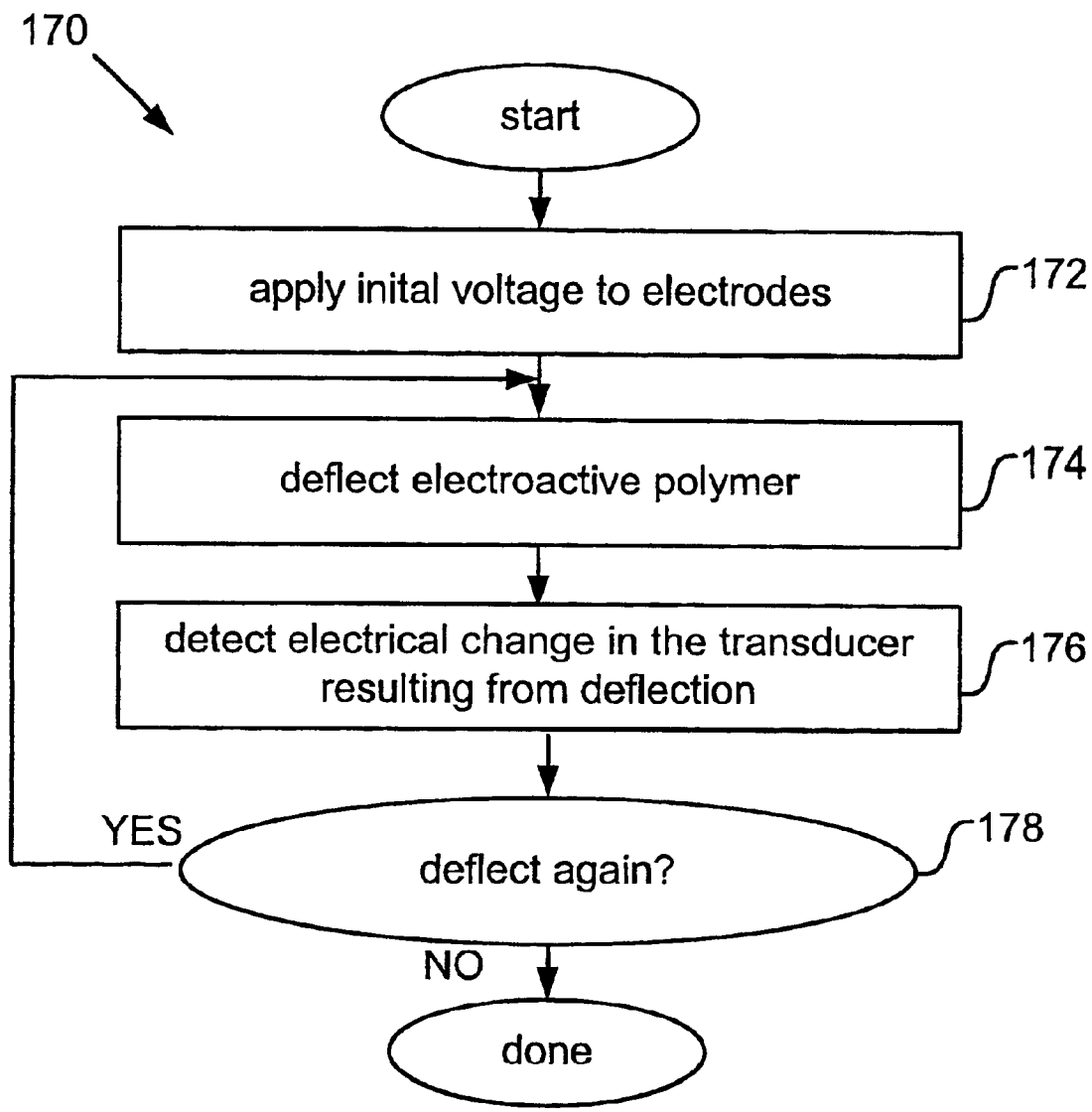
FIG. 4 illustrates an exemplary process flow for using an electroactive polymer transducer in accordance with one embodiment of the present invention.

FIG. 4 illustrates an exemplary process flow 170 for using an electroactive polymer transducer in accordance with one embodiment of the present invention. The transducer includes at least two electrodes in electrical communication with an electroactive polymer. The process flow 170 may take place in a sensor such as sensor 150 of FIG. 3A. Processes in accordance with the present invention may include up to several additional steps not described or illustrated here in order not to obscure the present invention. While sensing will now be described as a method, those skilled in the area will recognize that the present invention encompasses a system or device having units capable of performing the actions as described below.

Process flow 170 begins by applying an initial voltage to the electrodes of the transducer while it rests at some first position (172). The first position may correspond to the resting position of the electroactive polymer transducer sensor as it waits for input energy from an object being sensed. For example, the polymer may be mechanically coupled (e.g., using an adhesive) to a person's chest to measure expansion and contraction of the chest. The voltage applied may vary, but it is typically large enough such that noise in the electrical system does not compromise sensing. In a specific embodiment, a low voltage in the range of about 1 to 15V is applied as the initial voltage.

In one embodiment, the electroactive polymer is deflected before applying the initial voltage. This non-sensing deflection may correspond to pre-strain of the polymer (as described below in Section 5), or an actuation of the polymer when the transducer is also used in actuation mode (as described below in Section 8). For use with actuation, the initial voltage applied between the electrodes (172) is less than the voltage required to actuate the electroactive polymer.

Subsequently, the electroactive polymer is deflected from a first position to a second position (174). The deflection may result from a mechanical force applied to the polymer that inputs mechanical energy. For example, an expanding surface coupled to the polymer, such as a heating tank, may provide the mechanical force and mechanical deflection energy. In another embodiment, the deflection results from changes in electrical energy as supplied from an external electrical energy source, such as a portion of a circuit whose voltages are being measured. The electrical energy is applied to the polymer using one or more conductors that electrically communicate with the external electrical energy source. In this case, the transducer converts the external electrical energy changes in the circuit to deflection of the polymer.

The electrical change in the transducer resulting from deflection from the first position to the second position is detected by sensing electronics in electrical communication with the electrodes (176). The electrical change may be detected according an impedance change and/or a resistance change in the transducer. The electrical change may then be quantified and converted to deflection of the polymer using a logic device e.g., a single chip computer or microprocessor in electrical communication with the sensing electronics. The steps of deflection (174) and electrical energy detection (176) may then be repeated (178), is desired, to measure further changes in the parameter being sensed.

It should be noted that although the process flow 170 is described here as discrete steps, it is understood that continuous sensing using a sensor of the present invention is also possible.

5. Electroactive Polymers

In one embodiment, materials suitable for use as an electroactive polymer with the present invention may include any substantially insulating polymer or rubber (or combination thereof) that deforms in response to an electrostatic force or whose deformation results in a measurable electric change. One suitable material is NuSil CF19-2186 as provided by NuSil Technology of Carpenteria, Calif. Other exemplary materials suitable for use include silicone elastomers such as those provided by Dow Corning of Midland, Mich., acrylic elastomers, polyurethanes, thermoplastic elastomers, copolymers comprising PVDF, fluoroelastomers, and the like. Combinations of some of these materials may also be used as the electroactive polymer in transducers of this invention.

An electroactive polymer of the present invention may have a wide range of thicknesses. In one embodiment, polymer thickness may range between about 1 micrometer and 2 millimeters. Polymer thickness may be reduced by stretching the film in one or both planar directions. In many cases, electroactive polymers of the present invention may be fabricated and implemented as thin films. Thicknesses suitable for these thin films may be below 100 micrometers. The electroactive polymer films may also be laminated to other polymer films that provide support or protection. These supporting films may be from any of the classes described in the proceeding paragraph or may be other elastomeric materials.

Although the discussion so far has focused primarily on one type of electroactive polymer commonly referred to as dielectric elastomers (polymer 102 of FIG. 2A), sensors of the present invention may also incorporate other electroactive polymers. As the term is used herein, an electroactive polymer refers to a polymer that responds to electrical stimulation. Other common classes of electroactive polymer suitable for use with some embodiments of the present invention include electrostrictive polymers, and conductive polymers.

Electrostrictive polymers are conventionally described as polymers with an intrinsic strain response proportional to the square of the electric field. For the sensing applications described here, however, these and other variable dielectric materials can best be described as having variable dielectric "constants". That is, the electric polarization of the material depends in a non-linear way on the electric field. Such materials can be used in the present invention provided the capacitance formula takes into account the fact that the dielectric "constant" itself depends on the electric field, or more simply by measuring an empirical relation between capacitance and polymer deflection. Similarly, other electroactive polymer materials may be used. These include polymers that exhibit the piezoelectric effect (such as PVDF and various copolymers). In operational modes where the resistance or capacitance of the polymer is being measuremed, it is not the piezoelectric effect per se that is not providing the measurement.

Conductive polymers are polymers that can conduct electricity. Conductive polymers include electronically conductive polymers as well as ionically conductive polymers. Numerous examples of each type are known in the literature. Conductive polymers may be used in the present invention using the leakage method described below. They may also be used with variable resistance electrodes, circuits that measure electrical impedance (a combination of capacitance and resistance of the transducer), or capacitance. However, conductive polymers are often designed to have relatively low electrical resistance so that methods and circuits measuring, for example, capacitance, must be appropriate for the polymer resistance used as described above.

In one embodiment, an electroactive polymer of the present invention is pre-strained. Pre-strain of a polymer may be described, in one or more directions, as the change in dimension in a direction after pre-straining relative to the dimension in that direction before pre-straining. The pre-strain may comprise elastic deformation of polymer 102 and be formed, for example, by stretching the polymer in tension and fixing one or more of the edges while stretched. For many polymers, pre-strain increases the maximum amount of energy conversion between electrical and mechanical energy. It also allows for the production of thin uniform films which allows for operation at reduced voltages. In one embodiment, pre-strain improves the dielectric strength of the polymer. In another embodiment, the pre-strain is elastic. After actuation, an elastically pre-strained polymer could, in principle, be unfixed and return to its original state. The pre-strain may be imposed at the boundaries using a rigid frame or may also be implemented locally for a portion of the polymer.

In one embodiment, pre-strain is applied uniformly over a portion of polymer 102 to produce an isotropic pre-strained polymer. For example, an acrylic elastomeric polymer may be stretched by 200 to 400 percent in both planar directions. In another embodiment, pre-strain is applied unequally in different directions for a portion of polymer 102 to produce an anisotropic pre-strained polymer. Generally, after the polymer is pre-strained, it may be fixed to one or more objects. Each object is preferably suitably stiff to maintain the level of pre-strain desired in the polymer. The polymer may be fixed to the one or more objects according to any conventional method known in the art such as a chemical adhesive, an adhesive layer or material, mechanical attachment, etc. Pre-strain suitable for use with the present invention is further described in copending U.S. patent application Ser. No. 09/619,848, which is incorporated by reference for all purposes.

Sensors of the present invention are not limited to any particular shape, geometry, or type of transducer deflection. For example, a polymer and electrodes may be formed into any geometry or shape including tubes and rolls, stretched polymers attached between multiple rigid structures, stretched polymers attached across a frame of any geometry-including curved or complex geometries, across a frame having one or more joints, etc. Deflection of a transducer according to the present invention includes linear expansion and compression in one or more directions, bending, axial deflection in the case of a rolled polymer, deflection into or out of a hole provided on a substrate, etc. Deflection of a transducer may be affected by how the polymer is constrained by a frame or rigid structures attached to the polymer. Deflection may also be produced by use of a separate coupling mechanism. This mechanism can be a mechanical linkage or a fluid-filled chamber that applies a pressure on a region of the polymer.

In some cases, electrodes 104 and 106 cover a limited portion of polymer 102 relative to the total area of the polymer. This may be done to prevent electrical breakdown around the edge of polymer 102 or to achieve customized deflections for one or more portions of the polymer. As the term is used herein, an active area is defined as a portion of a transducer comprising polymer material 102 located between at least two electrodes.

Figure 5A:
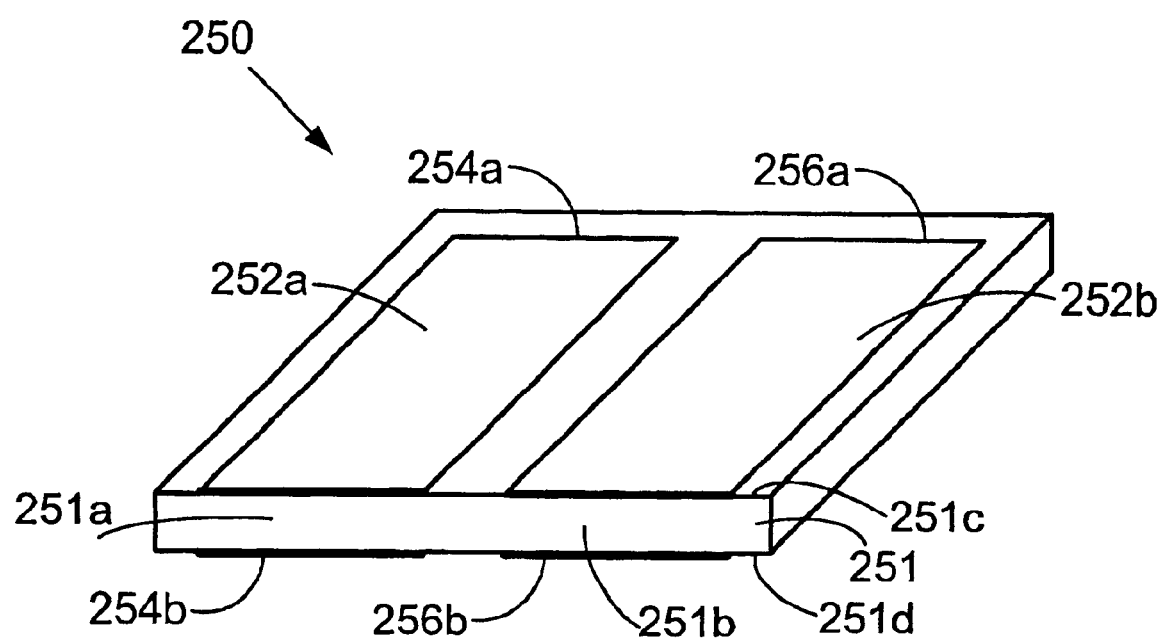
FIG. 5A illustrates a monolithic transducer comprising a plurality of active areas in accordance with one sensor embodiment of the present invention.

In accordance with the present invention, the term "monolithic" is used herein to refer to electroactive polymers, transducers, and devices comprising a plurality of active areas on a single electroactive polymer. FIG. 5A illustrates a monolithic transducer 250 comprising a plurality of active areas in accordance with one sensor embodiment of the present invention. The monolithic transducer 250 converts between electrical energy and mechanical energy. The monolithic transducer 250 comprises an electroactive polymer 251 including two active areas 252a and 252b. The polymer 251 can be held using, for example, a rigid frame (not shown) attached at the edges of the polymer 251.

The active area 252a has top and bottom electrodes 254a and 254b attached to the polymer 251 on its top and bottom surfaces 251c and 251d, respectively. The electrodes 254a and 254b provide and/or receive a voltage difference across a portion 251a of the polymer 251.

When sensing, deflection of the portion 251a causes a change in electric energy that is received by the electrodes 254a and 254b. As will be described in further detail below, transducers of the present invention may be used in multiple modes of operation including generation and actuation. For actuation, portion 251a deflects with a change in electric field provided by the electrodes 254a and 254b this field compresses the polymer 251 between the electrodes 254a and 254b and any other portions of the polymer 251 having sufficient electrostatic force to enable deflection upon application of voltages using the electrodes 254a and 254b. Active area 252b has top and bottom electrodes 256a and 256b attached to the polymer 251 on its top and bottom surfaces 251c and 251d, respectively. The electrodes 256a and 256b provide and/or receive a voltage difference across a portion 251b of the polymer 251.

Active areas for monolithic polymers and transducers of the present invention may be flexibly arranged in a variety of ways. In one embodiment, a transducer of the present invention includes a plurality of symmetrically arranged active areas. Further description of monolithic transducers suitable for use with the present invention are further described in commonly owned U.S. patent application Ser. No. 09/779,203, which is incorporated by reference herein for all purposes.

6. Electrodes

Generally, electrodes suitable for use with the present invention may be of any shape and material provided that they are able to supply or receive a suitable voltage to or from an electroactive polymer. The voltage may be either constant or varying over time. In one embodiment, the electrodes adhere to a surface of the polymer. As electroactive polymers of the present invention may deflect at high strains, electrodes attached to the polymers should also deflect without compromising mechanical or electrical performance. Correspondingly, the present invention may include compliant electrodes that conform to the changing shape of an electroactive polymer to which they are attached. The electrodes may be only applied to a portion of an electroactive polymer and define an active area according to their geometry.

In one embodiment, compliant electrodes of the present invention comprise a conductive grease such as carbon grease or silver grease. The conductive grease provides compliance in multiple directions. Particles may be added to increase the conductivity of the electrodes. By way of example, carbon particles may be combined with a polymer binder such as silicone to produce a carbon grease that has low elasticity and high conductivity. Other materials may be blended into the conductive grease to alter one or more material properties.

Compliant electrodes of the present invention may also include those made from colloidal suspensions. Colloidal suspensions contain submicrometer sized particles, such as graphite, silver and gold, in a liquid vehicle. Generally speaking, any colloidal suspension having sufficient loading of conductive particles may be used as an electrode. In a specific embodiment, a conductive grease including colloidal sized conductive particles is mixed with a conductive silicone including colloidal sized conductive particles in a silicone binder to produce a colloidal suspension that cures to form a conductive semi-solid. An advantage of colloidal suspensions is that they may be patterned on the surface of a polymer by spraying, dip coating and other techniques that allow for a thin uniform coating of a liquid. To facilitate adhesion between the polymer and an electrode, a binder may be added to the electrode. By way of example, a water-based latex rubber or silicone may be added as a binder to a colloidal suspension including graphite. Colloidal suspensions may also be patterned on a surface followed by evaporation of the liquid vehicle. The remaining conductive particles provide sufficient conductivity and, due to their small size, adhere to the surface.

In another embodiment, compliant electrodes are achieved using a high aspect ratio conductive material such as carbon fibrils or carbon nanotubes. These high aspect ratio carbon materials may form high surface conductivities in thin layers. High aspect ratio carbon materials may impart high conductivity to the surface of the polymer at relatively low electrode thicknesses due to the high interconnectivity of the high aspect ratio carbon materials. By way of example, thicknesses for electrodes made with common forms of carbon that are not high-aspect ratio may be in the range of 5–50 micrometers while thicknesses for electrodes made with carbon fibril or carbon nanotube electrodes may be less than 2–4 micrometers. Area expansions well over 100 percent in multiple directions are suitable with carbon fibril and carbon nanotube electrodes on acrylic and other polymers. High aspect ratio carbon materials may include the use of a polymer binder to increase adhesion with the electroactive polymer layer. Advantageously, the use of polymer binder allows a specific binder to be selected based on adhesion with a particular electroactive polymer layer and based on elastic and mechanical properties of the polymer.

In another embodiment, mixtures of ionically conductive materials may be used for the compliant electrodes. This may include, for example, water based polymer materials such as glycerol or salt in gelatin, iodine-doped natural rubbers and water-based emulsions to which organic salts such as potassium iodide are added. For hydrophobic electroactive polymers that may not adhere well to a water based electrode, the surface of the polymer may be pretreated by plasma etching or with a fine powder such as graphite or carbon black to increase adherence.

Various other types of electrodes suitable for use with the present invention are described in copending U.S. patent application Ser. No. 09/619,848, which was previously incorporated by reference above. Electrodes described therein that are suitable for use with sensors of the present invention include structured electrodes comprising metal traces and charge distribution layers and textured electrodes comprising varying out of plane dimensions.

Materials used for electrodes of the present invention may vary. Suitable materials used in an electrode may include graphite, carbon black, colloidal suspensions, thin metals including silver and gold, silver filled and carbon filled gels and polymers, and ionically or electrically conductive polymers. In a specific embodiment, an electrode suitable for use with the present invention comprises 80 percent carbon grease and 20 percent carbon black in a silicone rubber binder such as Stockwell RTV60-CON as produced by Stockwell Rubber Co. Inc. of Philadelphia, Pa. The carbon grease is of the type such as NyoGel 756G as provided by Nye Lubricant Inc. of Fairhaven, Mass. The conductive grease may also be mixed with an elastomer, such as silicon elastomer RTV 118 as produced by General Electric of Waterford, N.Y., to provide a gel-like conductive grease.

7. Electroactive Polymer Sensor Devices

An electroactive polymer sensor can be configured in a variety of ways to measure deflection or changes in a property or parameter being sensed. One common implementation of an electroactive polymer transducer is within a device. The device often employs mechanical coupling between the polymer and the object being sensed. Generally speaking, sensors of the present invention may be implemented with a variety of devices—including conventional devices retrofitted with an electroactive polymer and custom devices specially designed for one or more polymer sensors. Conventional devices include extenders, bending beams, stacks, diaphragms, etc. Several different exemplary devices suitable for use with sensors of the present invention will now be discussed.

Figure 5B:
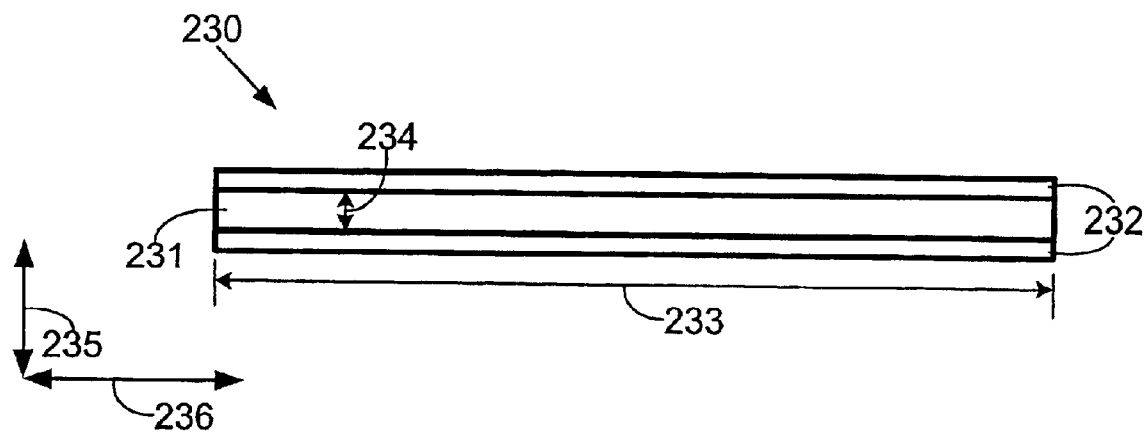
FIGS. 5B and 5C illustrate a linear sensor before and after external mechanical deflection in accordance with a specific embodiment of the present invention.
Figure 5C:
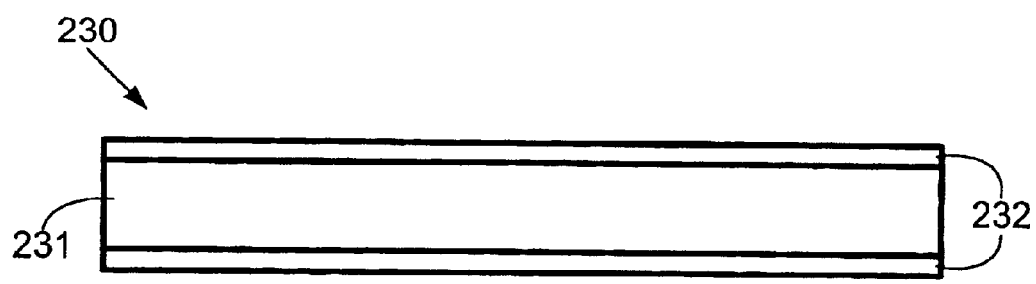

A straightforward electroactive polymer based sensor is one where an electroactive polymer transducer detects linear deflection in much the same way as a conventional linear strain gauge is employed. FIGS. 5B and 5C illustrate a linear sensor 230 before and after external mechanical deflection in accordance with a specific embodiment of the present invention. The linear sensor 230 is a planar mechanism allowing mechanical deflection sensing in one dimension 235. The linear sensor 230 comprises a polymer 231 having a length 233 substantially greater than its width 234 (e.g., an aspect ratio of at least about 4:1). The polymer 231 is attached on opposite sides along its length 233 to stiff members 232, which have a greater stiffness than polymer 231. Attached to opposite (top and bottom) surfaces of polymer 231 are electrodes (bottom electrode on bottom side of polymer 231 not shown) to provide and receive electrical energy to or from polymer 231. Leads may also extend from the electrodes for electrical communication with linear sensor 230.

The geometric edge constraint provided by the stiff members 232 substantially prevents displacement in a dimension 236 along the polymer length 233 and allows deflection almost exclusively in dimension 235. The stiff members 232 also allow external attachment to an object whose deflection is being measured, thus allowing sensor 230 to be used as a strain gauge for a linearly deflecting object. Commonly, the object produces the input energy associated with the change in a parameter being sensed and transfers the energy to polymer 231 using stiff members 232. Since the polymer 231 is flexible about its axis parallel to the stiff members 232, the linear sensor 230 may also be used to measure deflection of non-flat structures such as radial expansion and contraction of cylindrical surfaces.

In another embodiment, electroactive polymers suitable for use the present invention may be rolled or folded into linear sensors that deflect axially while converting between mechanical energy and electrical energy. Rolled or folded transducers and sensors typically include two or more layers of polymer. Rolled or folded sensors are applicable wherever linear actuators are used.

For some devices, stiffeners are added to an electroactive polymer sensor to limit deflection in one direction. For example, thin stiffening strips may be oriented perpendicular to a desired direction of measured strain and prevent strain in that transverse direction. The stiffeners help protect against changes in resistance or capacitance in the non-measured direction. An electroactive polymer sensor may then be wrapped around an object to measure a change in shape. The stiffeners also minimize "hot spots" or highly localized areas of strain where the object being measured might locally deform the sensor.

Figure 5D:
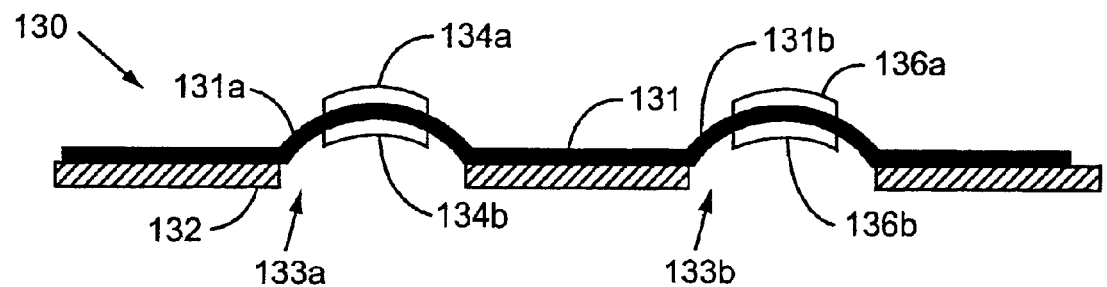
FIGS. 5D and 5E illustrate a cross-sectional side view of a monolithic 'diaphragm' sensor comprising a monolithic polymer before and after externally induced deflection in accordance with one embodiment of the present invention.
Figure 5E:
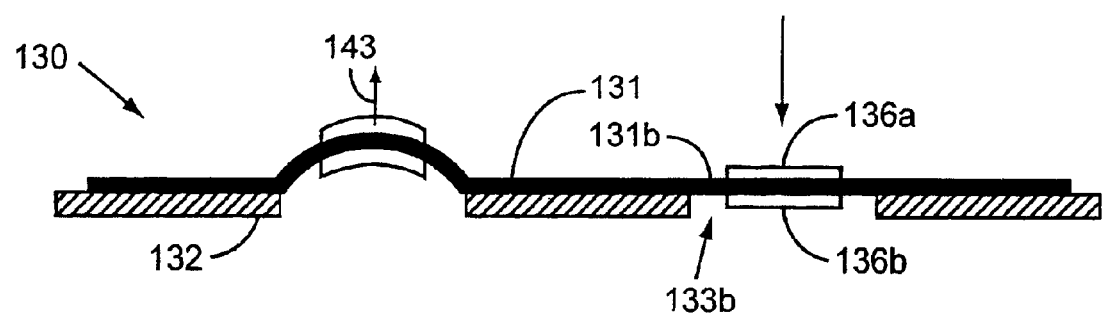

FIGS. 5D–E illustrate a cross-sectional side view of a monolithic 'diaphragm' sensor 130 comprising a monolithic polymer 131 before and after externally-induced deflection in accordance with one embodiment of the present invention. The polymer 131 is attached to a frame 132. The frame 132 includes apertures 133a and 133b that allow deflection of polymer portions 131a and 131b perpendicular to the area of the apertures 133a and 133b, respectively. The diaphragm sensor 130 includes electrodes 134a and 134b attached on either side of the portion 131a to provide or receive electrical energy to or from portion 131a and electrodes 136a and 136b attached on either side of the portion 131b to provide or receive electrical energy to or from portion 131b. Electrodes 134 and 136 are compliant and change shape with polymer 131 as it deflects.

Polymer portions 131a and 131b are configured to sense external mechanical input (a force or pressure over all or part of the area of the aperture) perpendicular to the area of the apertures 133a and 133b, respectively. In the waiting configuration of FIG. 5D, polymer portions 131a and 131b are actuated to the position shown, and external mechanical input which deviates either polymer portions 131a and 131b from their waiting position causes an electrical change that is received by their respective electrodes.

Using electrodes 134 and 136, portions 131a and 131b are capable of independent sensing. As illustrated in FIG. 5E, upon application of an external mechanical input to portion 131a to deflect the portion downward, the deflection produces a capacitance or resistance change (depending on the transducer) in the polymer portion 131a or electrodes 134a and 134b that is received by electrodes 134a and 134b. Each of the portions 131a and 131b is capable of sensing expansion and contraction in both perpendicular directions-upwards or downwards—relative to the plane.

Diaphragm sensor 130 is well suited for use as a contact sensor. In one embodiment, diaphragm sensor 130 is implemented within a keyboard and comprises between 30 and 150 portions 131. Each portion 131 is used as a keystroke contact sensor for a key on the keyboard. Diaphragm sensor 130 may also be used to measure a force or pressure on polymer 131. For example, sensor 130 may comprise a rectangular array of 20–200 portions 131a and 131b across a planar surface and the sensor may be implemented to measure air flow over the sensor 130 surface. Since each portion provides independent feedback or air flow local to the portion, the sensor 130 then may provide a distributed profile for air flow over its surface.

Although FIGS. 5B–5E illustrate two exemplary devices suitable for use with sensors of the present invention, other devices including one or more electroactive polymers may also be employed. Other exemplary devices, such as bending beam devices, are also suitable for use with the present invention. Additional exemplary linear and non-linear devices suitable for use with the present invention are described in commonly owned U.S. patent application Ser. No. 09/619,848, which was previously incorporated by reference.

In one embodiment, the sensor device is mechanically coupled to the object whose parameter is changing. Rigid members included in the sensor device are attached to the transducer to allow mechanical coupling and directly apply dimensional changes from the object to induce deflection of the polymer. When the object produces energy associated with the parameter change, the coupling mechanism receives the energy associated with the parameter change and transfers a portion of the energy to the electroactive polymer (typically enough to deflect the polymer). In some cases, the electroactive polymer sensor is an integral part of the inherent structure of an object whose shape or size is being measured. This intimate contact with the object allows electroactive polymer sensors of the present invention to be used as strain gauge sensors for objects they are attached to. There are countless applications for strain gauge sensors. In one embodiment, electroactive polymer sensors of the present invention may sense a quantity or item detected from the environment around the sensor, e.g., ambient air temperature.

Alternatively, the changing parameter being measured by the sensor corresponds to a changing property of the electroactive polymer included in the sensor, e.g. displacement of the polymer, and no coupling mechanism is used. For example, the sensor may be configured to measure displacement of an electroactive polymer used for actuation as will be described in further detail below.

In one embodiment, a sensor of the present invention detects and measures changes in an electrical property. In this case, an electrical coupling mechanism is used to transfer electrical energy associated with the changing electrical property onto the electroactive polymer. The electrical energy causes the polymer to deflect, and this deflection is measured by the electrodes as described above. In a specific embodiment, a conductive element is included in the sensor device and is in electrical communication with the electroactive polymer. Voltage received by the conductive element cause the electroactive polymer to deflect, and the deflection is detected and measured by an electronic circuit in electrical communication with electrodes 104 and 106.

8. Multifunctionality

For ease of understanding, the present invention has mainly been described and shown by focusing on a single form of electroactive polymer operation—when the transducer is operating as a sensor. However, electroactive polymer transducers have other functional uses such as actuation and generation. In one aspect, sensors of the present invention may be integrated with other electroactive polymer functions. Electroactive polymer transducers configured to have more than one function is referred to herein as 'multifunctional'.

FIGS. 2A and 2B may be also used to show one manner in which the transducer portion 100 converts electrical energy to mechanical energy. Polymer 102 may deflect with a change in electric field provided by the top and bottom electrodes 104 and 106. Deflection of the transducer portion 100 in response to a change in electric field provided by the electrodes 104 and 106 is referred to as 'actuation'. For actuation, a change in electric field corresponding to the voltage difference applied to the electrodes 104 and 106 produces mechanical pressure within polymer 102. In this case, the unlike electrical charges produced by electrodes 104 and 106 attract each other and provide a compressive force between electrodes 104 and 106 and an expansion force on polymer 102 in planar directions 108 and 110, causing polymer 102 to compress between electrodes 104 and 106 and expand in the planar directions 108 and 110. As polymer 102 changes in shape, the deflection may be used to produce mechanical work.

For actuation, the transducer portion 100 generally continues to deflect until mechanical forces balance the electrostatic forces driving the deflection. The mechanical forces include elastic restoring forces of the polymer 102 material, the compliance of electrodes 104 and 106, and any external resistance provided by a device and/or load coupled to the transducer portion 100, etc. The deflection of the transducer portion 100 as a result of an applied voltage may also depend on a number of other factors such as the polymer 102 dielectric constant and the size of polymer 102.

Some sensors of the present invention may also be configured or designed for use as an actuator to produce mechanical output in addition to sensing. In this case, the electroactive polymer is also arranged in a manner which causes a portion of the polymer to deflect in response to a change in electric field provided by the at least two electrodes. Alternatively, the present invention also applies to conventional electroactive polymer devices operating as an actuator and further configured in electrical communication with sensing electronics as described above and able to receive electrical energy in a sensing mode. Suitable electroactive polymer actuators are further described in Ser. No. 09/619,848, which was previously incorporated by reference.

Another common electroactive polymer transducer function is converting mechanical to electrical energy—or generation. The mechanical energy may be harvested from a biological source such as walking energy harvested from a human being. Thus, some sensors of the present invention may also be configured or designed for use as a generator to produce electrical energy. Typically, a generator of the present invention comprises a polymer arranged in a manner that causes a change in electric field in response to deflection of a portion of the polymer. The change in electric field, along with changes in the polymer dimension in the direction of the field, produces an increase in voltage, and hence an increase in electrical energy. The increase in electrical energy may be harvested and stored by generation circuitry in electrical communication with the electrodes. Suitable electroactive polymer generator circuits are further described in Ser. No. 09/792,877, which is incorporated herein by reference for all purposes.

In one aspect, transducers of the present invention may be used as an actuator to convert from electrical to mechanical energy, a generator to convert from mechanical to electrical energy, a sensor to detect changes in a parameter, or any combination thereof. In all the figures and discussions for the present invention, it is important to note that the polymers and devices may convert between electrical energy and mechanical energy bi-directionally.

For a transducer having a substantially uniform thickness, one method for determining the function of the transducer, or a portion of the transducer associated with a single active area, as being an actuator, sensor, or generator, is to consider the change in net area orthogonal to the thickness associated with the polymer deflection. For these transducers or active areas, when the deflection causes the net area of the transducer/active area to decrease and there is charge on the electrodes, the transducer/active area is converting from mechanical to electrical energy and acting as a generator or sensor. Conversely, when the deflection causes the net area of the transducer/active area to increase and charge is on the electrodes, the transducer/active area is converting electrical to mechanical energy and acting as an actuator or sensor. The change in area in both cases corresponds to an inverse change in film thickness, i.e. the thickness contracts when the planar area expands, and the thickness expands when the planar area contracts. Both the change in area and change in thickness determine the amount of energy that is converted between electrical and mechanical. Since the effects due to a change in area and corresponding change in thickness are complementary, only the change in area is discussed herein for sake of brevity. In addition, although deflection of an electroactive polymer is primarily discussed herein as a net increase in area of the polymer when the polymer is being used in an actuator to produce mechanical energy, it is understood that in some cases (i.e. depending on the loading), the net area may decrease to produce mechanical work. Thus, sensors of the present invention may include both actuator and generator modes, depending on how the polymer is arranged and applied.

When used for actuation, suitable actuation voltages for electroactive polymers, or portions thereof, may vary based on the material properties of the electroactive polymer (e.g., dielectric constant) and the dimensions of the polymer (e.g., polymer film thickness). For example, actuation electric fields used to actuate polymer 102 in FIG. 2A may range in magnitude from about 0 V/m to about 440 MV/m. Actuation electric fields in this range may produce a pressure in the range of about 0 Pa to about 10 MPa. In order for the transducer to produce greater forces, the thickness of the polymer layer may be increased. Actuation voltages for a particular polymer may be reduced by increasing the dielectric constant, decreasing the polymer thickness, and decreasing the modulus of elasticity, for example.

A transducer may be configured such that sensing is performed simultaneously with actuation of the transducer. For a monolithic transducer, one active area may be responsible for actuation and another for sensing. Alternatively, the same active area of a polymer may be responsible for actuation and sensing. In this case, a lowamplitude, high frequency AC (sensing) signal may be superimposed on the driving (actuation) signal. For example, a 1000 Hz sensing signal may be superimposed on a 10 Hz actuation signal. The driving signal will depend on the application, or how fast the actuator is moving, but driving signals in the range from less than 0.1 Hz to about 1 million Hz are suitable for many applications. In one embodiment, the sensing signal is at least about 10 times faster than the motion being measured. Sensing electronics may then detect and measure the high frequency response of the polymer to allow sensor performance that does not interfere with polymer actuation. Similarly, if impedance changes are detected and measured while the electroactive polymer transducer is being used as a generator, a small, high-frequency AC signal may be superimposed on the lower-frequency generation voltage signal. Filtering techniques may then separate the measurement and power signals.

Figure 3D:
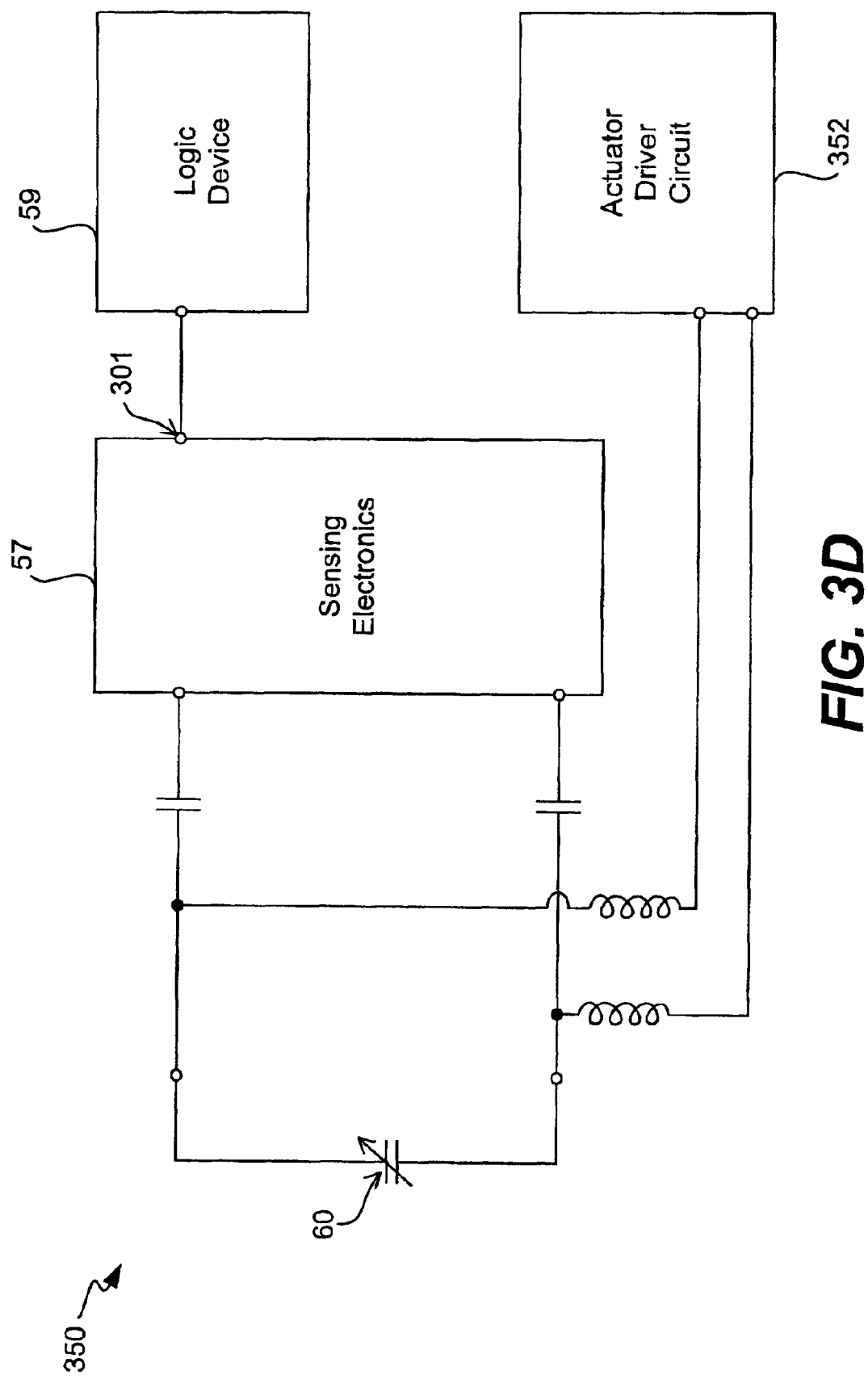
FIG. 3D illustrates circuitry for a multifunctional transducer in accordance with another embodiment of the present invention.

FIG. 3D is a specific example of a circuit 350 comprising connections suitable for use with a multifunctional electroactive polymer transducer 60. In this example, transducer 60 functions as an actuator and as a sensor. In addition to the sensing electronics (see FIG. 3C) and logic device 59, circuit 350 comprises an actuator driver circuit 362 for controlling actuation of transducer 60.

9. Applications

As the present invention includes sensors that may be implemented in both the micro and macro scales, implemented in any actuator or generator application where feedback is desirable, and implemented with a wide variety of sensor designs, the present invention finds use in a broad range of applications. Provided below are several exemplary sensing applications.

Generally, electroactive polymer sensors of this invention detect a "parameter" and/or changes in the parameter. The parameter is usually a physical property of an object such as its temperature, density, strain, deformation, velocity, location, contact, acceleration, vibration, volume, pressure, mass, opacity, concentration, chemical state, conductivity, magnetization, dielectric constant, size, etc.

In some cases, the parameter being sensed is associated with a physical "event". The physical event that is detected may be the attainment of a particular value or state of a physical or chemical property. Sensing electronics may provide the electrical signal to a logic device that signals attainment of the event based on the electrical energy change of the transducer. When the parameter being sensed is associated with multiple events, each event may be defined as a state of the object being sensed. The sensor may then be configured to detect each of the states. For example, a robotic gripper may have open and closed positions (e.g., powered by an on/off pneumatic source) and a linear electroactive polymer sensor, coupled to the gripper and in electrical communication with interface electronics, has a known electrical capacitance for deflection associated with the open and closed states of the gripper.

Applications for sensors of the present invention may be classified based upon the parameter being sensed. Many sensor classes are known and used for different applications. Specific sensor classes suitable for electroactive polymer usage include, pressure sensors, contact sensors, flow or volume sensors, stress/strain sensors, accelerometers, shock sensors, vibration sensors, alignment, and the like. In each case, a coupling mechanism may be used to convert the changing parameter to deflection of the polymer. Electroactive polymer sensors represent a simple, light weight, customizable, and efficient replacement for conventional sensors in any of these sensors classesMany examples of things to be sensed and sensing mechanisms are described by Julian W. Gardner in "Microsensors: Principles and Applications," John Wiley, 1994 (incorporated herein by reference in its entirety and for all purposes). Among the listed items are mechanical sensors: displacement, velocity, acceleration, force, torque, pressure, mass, flow, amplitude; thermal sensors: temperature, heat, heat flow, entropy, heat capacity; electrical sensors: charge, current, voltage, resistance, conductance, capacitance, inductance, dielectric permittivity, polarization, frequency, magnetic sensors: magnetic field, flux, magnetic moment, magnetization, magnetic permeability; and the like.

In the micro domain, electroactive polymer based sensors may range in thickness from several micrometers to several millimeters, and preferably from several micrometers to hundreds of micrometers. In one embodiment, the area of the sensor is less than 10E-8 $m^2$. [e.g., 100 microns×100 microns] Micro electroactive polymer based sensors in this size range are well-suited for sensing in micro robotic applications. This may include detecting the position or state of micro robot legs, grippers, pointing mirror actuators for CCD cameras, wire feeders for micro welding and repair, clamping actuators to hold rigid positions, position of microoptical components, position of microvalves, and high-resolution tactile skins. Micro scale diaphragms or related configurations may also be used for measuring small volumes of liquid, for example for drug dispensing or micro fluidic applications.

In the macro domain, electroactive polymer sensors are well suited for use in applications such as robotics and linear actuators. In these applications, the electroactive polymer sensor is mechanically coupled to one or more objects that deflect the polymer. In a specific embodiment, the transducer acts as a mechanical strain sensor that converts mechanical deflection to electrical energy. Sensors of the present invention may also be used to measure the position of robotic manipulators and linkages of general automated machinery. The lightweight sensors are also particularly attractive for aerospace actuation applications where size and weight are important. These applications may also benefit from an electroactive polymer sensor that is compact, may be custom made in a variety of shapes and sizes, is environmentally robust, and is accurate. In automotive embodiments, sensors of the present invention are useful as force sensors and pressure sensors. One specific force sensing application employs electroactive polymer sensors applied within a seat to detect passenger presence, e.g., within a textile as described below.

Electroactive polymer sensors are well suited for use as pressure sensors in the macro domain. Diaphragm pressure sensors may include flow sensors (e.g., for fluids) and vibration sensors (e.g., a microphone).

A sensor of the present invention may be adapted to detect nearly any parameter (physical property, event, state, etc.) desired. Typically, this involves configuring or designing the electroactive polymer transducer based on the object or parameter being sensed. One of skill in the art will appreciate the numerous ways to implement sensors in a particular application.

The geometry of the electroactive polymer may be tailored to an application. For a tubular or rolled electroactive polymer sensor configured to detect axial linear strain, the thickness, width, and/or outer and inner tube diameter of the electroactive polymer may be chosen to provide the desired change in resistance or capacitance with axial linear strain.

The sensor may also be adapted to withstand the operating conditions to which it will be exposed and fit within good design practices including reliability, accuracy, size, weight, safety, and compatibility with other components and the application. For example, sensors implemented in an automotive application may be adapted to operate reliably under the variable temperature conditions of the automobile. Because applications in which sensors of the present invention are implemented may vary considerably and may include environmentally prohibitive conditions, specific features of a sensor may be governed by a particular application.

In one embodiment, electroactive polymer sensors of the present invention are passive in that they passively respond to energy input from the object or parameter being detected. In some cases, the sensor may be viewed as being energized by the quantity being sensed. For example, thermal energy may provide the energy to strain a structure mechanically coupled to the electroactive polymer sensor, and thereby provide the energy to deflect the polymer. These passive sensors may be implemented with a small battery that supplies an initial voltage only when triggered by energy from the object or parameter being detected. Further polymer deflection and change in electrical energy provided to the polymer may then be detected and sensed as described above.

In many other cases, sensors of the present invention are stand-alone, continually powered devices that provide real time measurements of the quantity being sensed. These types of sensors are often referred to as an 'active' sensor. These sensors may be implemented with their own battery or wiring to a central power source, and provide continual measurement of the parameter being sensed.

As described above, an electrical coupling mechanism, such as a conductor, may be employed in electrical communication with the transducer and in electrical communication with an object having a voltage to be measured. The conductor transmits electrical energy onto the transducer to induce deflection (using the ability of many electroactive polymers, including dielectric elastomers, to function as actuators) and allows a sensor of the present invention to detect changes in the voltage of the object.

Sensors of the present invention are also well suited to detect position and motion of moving objects. Examples include the detection and measurement of moving body parts and moving objects in automation. Exemplary biomedical applications that use measurement of moving body parts include plethysmography, pneumography, and kinesiology. In a specific embodiment, a sensor of the present invention is disposed circumferencially around a human chest and used as a respiration sensor that detects expansion and contraction of the chest. Exemplary computer applications that use measurement of moving body parts include computer input devices such as virtual reality gloves and joysticks.

Another implementation of the invention provides a distributed collection of sensors (e.g., an array) each including an electroactive polymer sensor. The individual sensors may be identical to or similar to any one of the sensors described above. In a specific embodiment, the plurality of electroactive polymer sensors are mounted at separate locations on a single structure, e.g., to measure strain of different portions of a large object such as a containment vessel, retaining wall, levee, or bridge.

Thinly rolled, tubular or linear electroactive polymer sensors may be interwoven or layered to produce fibrous transducers that measure strain in textiles or composites. In one embodiment, sensor arrays of the present invention are integrated into materials such as textiles and composites in order to provide information about bending or deflection of the material. Such a textile or composite is useful in a kinesiological measurement suit.

Figure 6A:
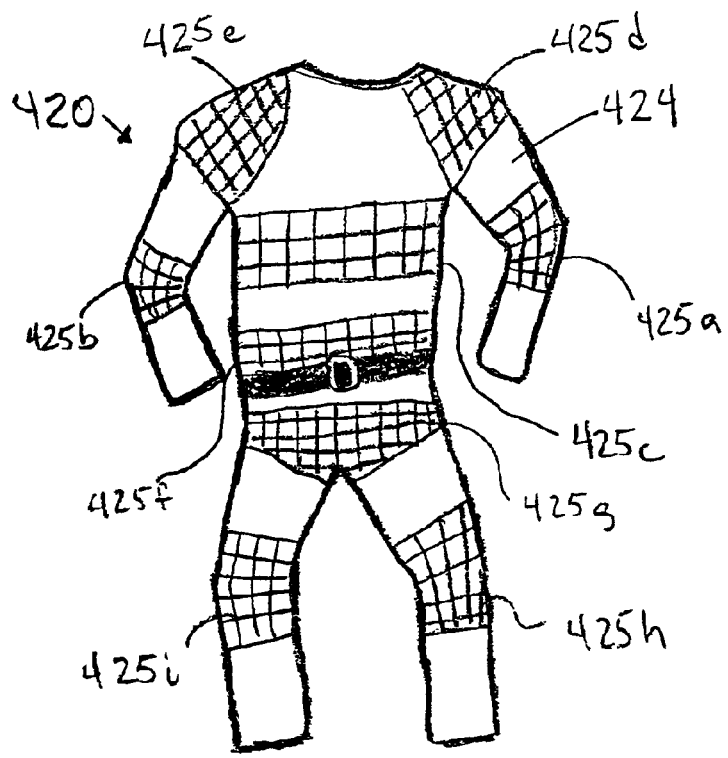
FIGS. 6A–6B illustrates a kinesiological measurement suit for monitoring movement of a person wearing the suit in accordance with a specific embodiment of the present invention.
Figure 6B:
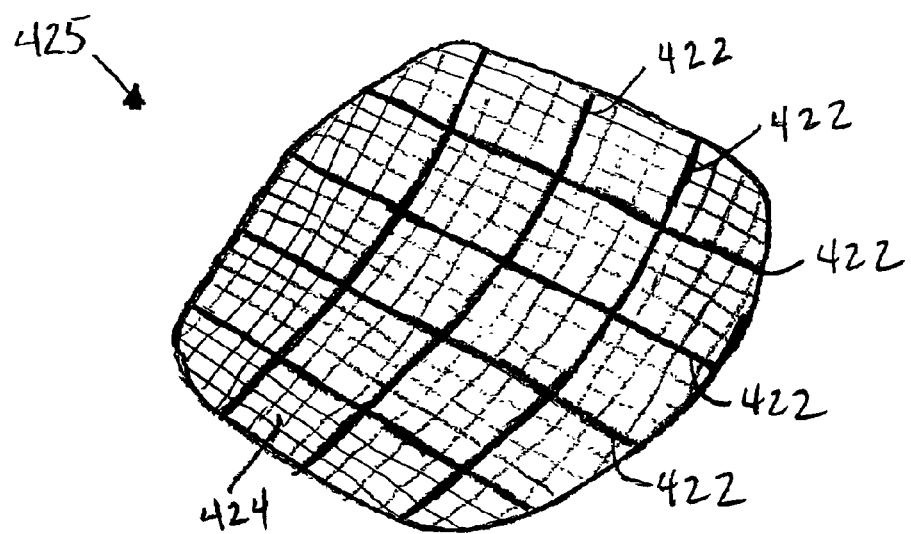

FIGS. 6A–6B illustrate a kinesiological measurement suit 420 for monitoring movement of a person wearing suit 420 in accordance with a specific embodiment of the present invention. Suit 420 includes a sensor array comprising interwoven electroactive polymer sensors 422 that measure one-dimensional strain along their longitudinal axis. The sensors 422 are woven back and forth through a section of fabric 424 or composite structure to provide interconnectivity of each sensor 422 with fabric 424. The sensors 422 are provided in interest areas 425 of suit 420 where deflection information is desired such as the elbows (425a and 425b), chest (425c), shoulders (425d and 425e), hip (425f), groin (425g), and knees (425h and 425i).

FIG. 6B shows a close-up view of one of the interest areas 425. When fabric 424 is strained in the direction of the sensor 422 segments, a large deflection signal is measured since the total deflection on each sensor 422 is multiplied by the number of times the sensor 422 crosses the fabric section. If strain measurement along several closely spaced lines is desired, electrical connections can be made to individual sensors 422 and the response from each may be independently processed. An interconnected network of fiber sensor 422 running in orthogonal directions may be used to give more complete strain information for flat fabrics and structures.

Collectively, several fibrous electroactive polymer sensors 422 may be used to detect motion of a feature included in the suit, e.g., an arm, using one or more of the interest areas 425. Suit 420 is well suited for human movement monitoring (e.g., of an astronaut) and computer input (e.g. for games). The fibrous design of FIGS. 6A–6B is also well suited for detecting bending and deflection in other applications such as a flexible robotic manipulator or flexible endoscope.

Figure 6C:
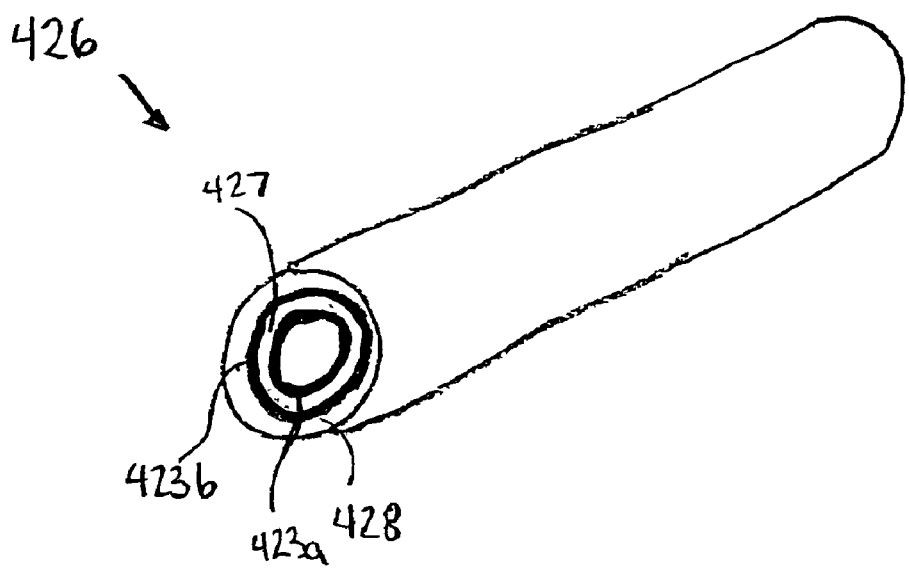
FIGS. 6C–F illustrate perspective cross sectional views of several fibrous electroactive polymer sensors suitable for use with the suit of FIG. 6A in accordance with specific embodiments of the present invention.

FIG. 6C illustrates a perspective cross sectional view of a fibrous electroactive polymer sensor 426 suitable for use as a sensor 422 in accordance with a specific embodiment of the present invention. Sensor 426 is tubular and comprises a tubular electroactive polymer 427 disposed on the inner surface of an insulating elastomer 428. Electrodes 423a and 423b are disposed on the inner and outer surfaces of polymer 426 and extend along the longitudinal length of sensor 426. The electrodes 423a and 423b provide electrical energy to the electroactive polymer transducer 426. Insulating elastomer 428 is flexible and surrounds polymer 427, and provides electrical insulation from the electrode on the outer surface of electroactive polymer 427. Longitudinal (i.e. axial) stretching of sensor 426 deflects polymer 427 and produces an increase in resistance of electrode 423b that is detected by sensing electronics in electrical communication with electrodes 423a and 423b.

Figure 6D:
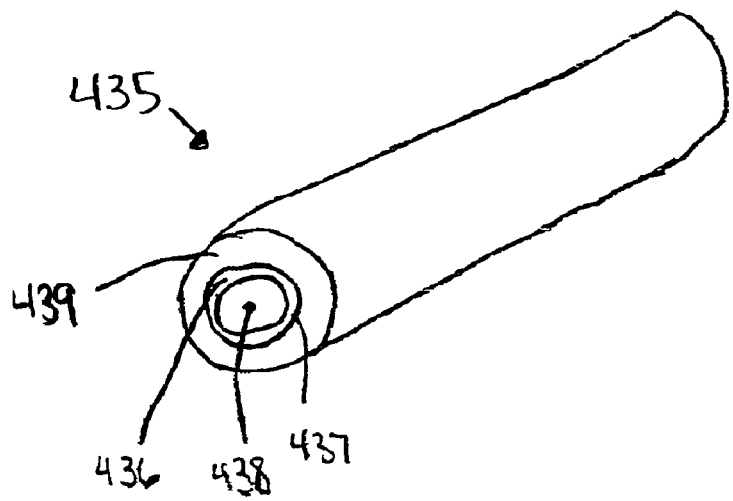

FIG. 6D illustrates a perspective cross sectional view of a fibrous electroactive polymer sensor 435 suitable for use as a sensor 422 in accordance with another specific embodiment of the present invention. Sensor 435 comprises a cylindrical electroactive polymer 436 core with an electrode 437 on the outer surface of electroactive polymer 436. A coiled wire or compliant conductive electrode (such as made using elastomer-carbon composites known in the prior art) 438 extends through the center of electroactive polymer 436 and acts as the second electrode for applying and receiving electrical energy to and from polymer 436. Insulating elastomer 439 is flexible and surrounds polymer 436, and provides electrical insulation from electrode 437 on the outer surface of electroactive polymer 436. Longitudinal stretching of sensor 435 deflects electrode 437 and produces a change in capacitance of polymer 436 that is detected by interface electronics in electrical communication with electrodes 437 and 438.

Figure 6E:
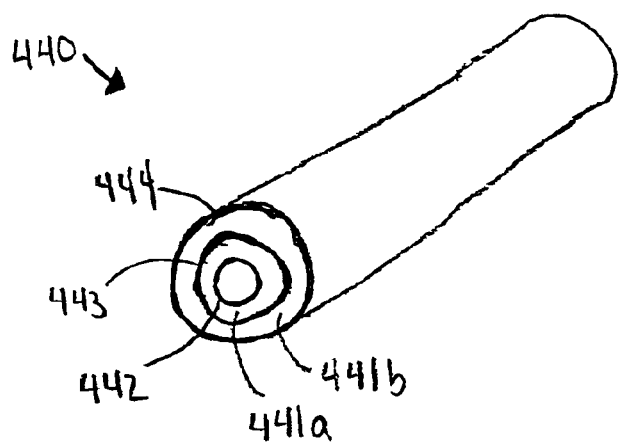

FIG. 6E illustrates a perspective cross sectional view of a fibrous electroactive polymer sensor 440 suitable for use as a sensor 422 in accordance with another specific embodiment of the present invention. Sensor 440 is coaxial and comprises tubular electroactive polymers 441a and 441b. Electrodes 442 and 443 are disposed on the inner and outer surfaces of electroactive polymer 441a, respectively, and provide or receive electrical energy from polymer 441a. Electrodes 443 and 444 are disposed on the inner and outer surfaces of electroactive polymer 441b, respectively, and provide or receive electrical energy from polymer 441b. Longitudinal stretching of sensor 440 deflects polymers 441a and 441b and produces an increase in capacitance of polymers 441a and 441b that is detected by sensing electronics in electrical communication with the electrodes 442, 443 and 444.

Alternately, the two polymers 441a and 441b can be used as independent sensors in conjunction with electrodes 442, 443, and 444. For example, polymer 441a can be used with its electrodes as a capacitive sensor and polymer 441b can be used with its electrodes as a leakage resistance sensor. In this way one may obtain two independent measurements of deflection using two different methods, and combine the measurements for higher overall accuracy. Alternately, the two measurements might be used for different conditions, for example one might be used for high speed deflections and the other for low speed deflections.

Figure 6F:
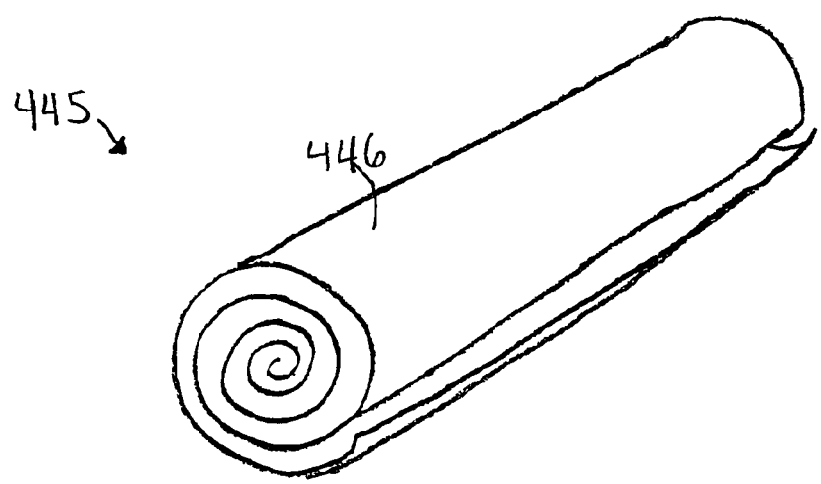

FIG. 6F illustrates a perspective cross sectional view of a fibrous electroactive polymer sensor 445 suitable for use as a sensor 422 in accordance with another specific embodiment of the present invention. Sensor 445 comprises a rolled electroactive polymer 446. The roll is formed from a multilayer stack 446 of film comprised of two or more layers of dielectric polymer, each with electrodes on both of its surfaces. It is possible to use any even number of layers of polymer in the multilayer stack. The reason for using an even number of layers is so that only electrodes of like polarity will make contact as the stack is rolled. Stretching of sensor 445 deflects polymer stack 446 and produces an increase in capacitance of polymer stack 446 that is detected by sensing electronics in electrical communication with electrodes of polymer 446.

Figure 6G:
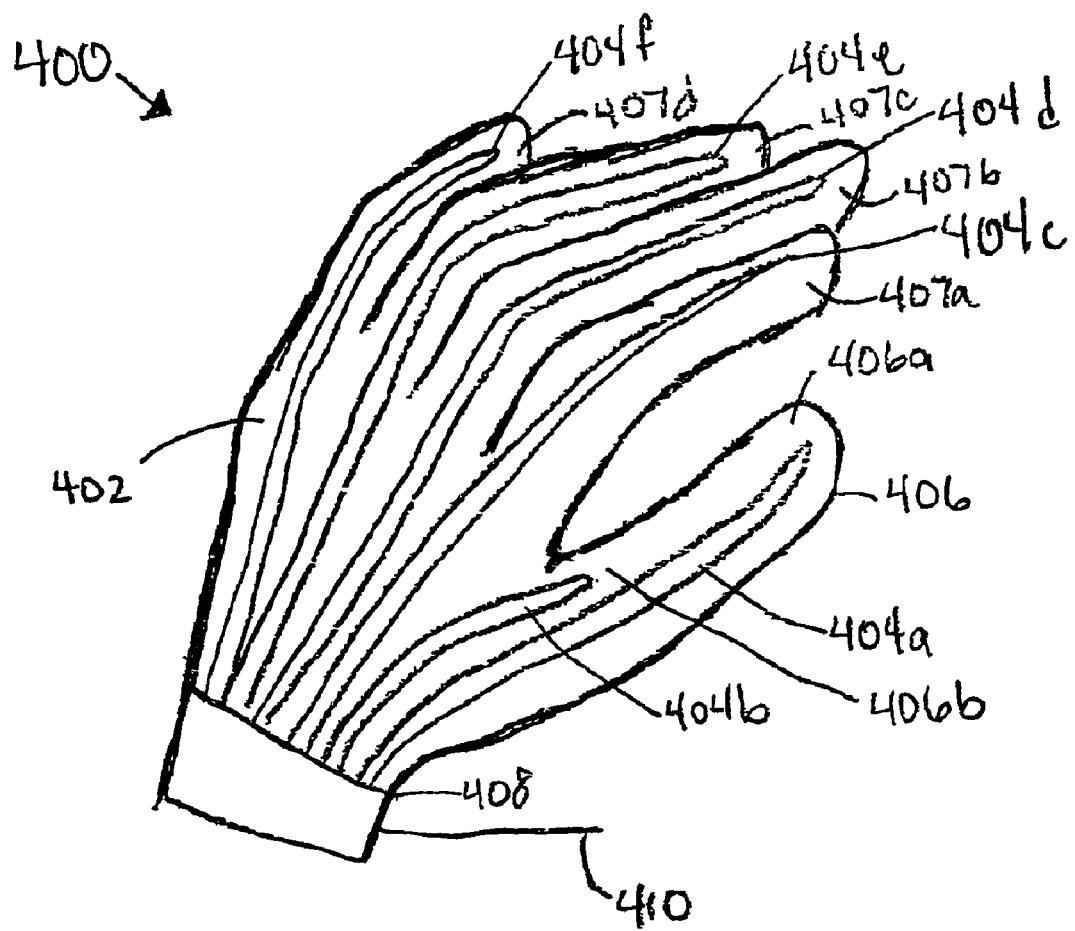
FIG. 6G illustrates a computer-input glove in accordance with another specific embodiment of the present invention.

FIG. 6G illustrates a computer input glove 400 in accordance with another specific embodiment of the present invention. Glove 400 includes a rubberized fabric 402 that provides flexible structure and also acts as an electroactive polymer. Electroactive polymer sensor portions 404 are defined by electrodes patterned on the outside (shown) and inside (not shown) surfaces of rubberized fabric 402. Thus, rubberized fabric 402 is a monolithic polymer as defined above and glove 400 comprises a sensor array disposed on a single electroactive polymer. In another embodiment, discrete and separate fiber sensors are adhered to a fabric 402.

Changes in resistance of sensor portions 404 indicate linear strain of portions of glove 400 in the immediate area of the sensor portion. For example, sensor portion 404a extends from a wrist 408 to the distal end 406a of thumb 406. Bending of thumb 406 stretches sensor portion 404a and causes an increase in resistance for the electroactive polymer sensor portion 404a. Wires 410 extend from wrist portion 408 and are in electrical communication with electrodes for each sensor portion 404 of glove 400. Wires 410 provide electrical communication with external interface electronics. Sensor portion 404b extends from wrist 408 to an intermediate portion 406b of thumb 406. Strain of sensor portion 404b allows position measurement of intermediate portion 406b of thumb 406; thus providing independent feedback for the distal end 406a and the intermediate joint of a user's thumb moving within glove 400. Sensors 404c–f extend from wrist 408 to a distal end of each finger 407a–d, respectively, and provide deflection and motion measurement for each finger. Taken together, the strain in formation for the thumb and fingers can be easily correlated to a position of the hand within the glove. This correlation allows the wearer to use gestures or sign language to interface with a computer, for example.

Electroactive polymer sensors of the present invention may also be included in an animated device, e.g., a robotic arm. As described above with respect to multifunctional actuators, the same electroactive polymer transducer that provides mechanical output in an animated device may also provide sensing capabilities. These multifunctional transducers may then be made into "smart transducers" that intrinsically incorporate position, force, tactile sensing, etc., into the robotic arm. These smart transducers may simplify feedback control of the actuator for an animated device, thus allowing for enhanced dexterity and controlled movement. These sensors are well suited for use in robotic or animatronic devices and toys.

In another embodiment, transducers of the present invention act as a haptic sensor for detecting touch on a robot. For example, an electroactive polymer sensor may be used to detect whether an animatronic face is in contact with an object. Sensing contact in this manner may be advantageous for toys that provide an interactive and automatic response with a user. Alternatively, numerous haptic sensors may be arranged under the skin of an animatronic device. Each of the haptic sensors then detects touch for a different body portion of the animated device. The same transducer may then be used for actuation in response to user interaction. For example, a haptic electroactive polymer sensor/actuator may be placed in the nose of a stuffed toy and the nose wiggles when touched (via actuation of the electroactive polymer). Alternatively, the stuffed toy may receive time varying force feedback from its environment and react accordingly. For example the stuffed toy may be a teddy bear that reactively pushes back when its paw is pushed. In a more elaborate design, the magnitude of reactive push is proportional to the force pushing on the paw. In another embodiment, automatic toy interaction is designed not to stop an action based on sensor feedback. For example, a toy dinosaur with biting capabilities powered by electroactive polymer transducers may use force feedback from the transducers to decide when not to keep biting.

Some sensors of the present invention are also well suited for prosthetic and medical applications where a biological parameter or parameter related to medical instrumentation is to be sensed. The biological parameter may include the strain displacement, or other time varying parameter, of a tissue such as bone, muscle, or skin. For example, a sensor may be mechanically and/or electrically coupled to a portion of a person's heart for detecting muscle strain, heart rate, pressure, etc. In this case, the sensor comprises a biological interface that allows coupling to the biological tissue. One of skill in the art is aware of techniques to interface a mechanical device with tissue and the like. Some sensors described herein are generally well suited for in vivo, ex vivo and in vitro usage. Alternately, some sensors are well suited for angioplasty applications where the sensor detects tool diameter, artery or vein diameter, or blood flow across the sensor.

10. Electroactive Polymer Sensor Arrays

Sensors of the present invention are also suitable for use in an array. Many applications require that numerous objects or changes in parameters be separately detected. For example, a keyboard requires contact detection for each key on the keyboard. Alternatively, a large structure may require sensing strain resulting from stress-induced operating conditions (e.g., temperature, for disparate parts of the structure). Thus, one embodiment employs a sensor array of at least two electroactive polymer transducer sensor for detecting a change in one or more parameters.

The sensor array comprises one or more electroactive polymer transducer sensors. In one embodiment, the sensor array uses a single monolithic electroactive polymer and different active areas of the monolithic polymer each sense a different parameter change. For example, the diaphragm sensor 130 of FIG. 5D is well suited for use as a keyboard contact sensor that detects contact (an event related to change in position of a key) for each key on the keyboard. In this case, electrodes on the monolithic electroactive polymer are patterned such that an active area and portion 131 of the polymer mates with each key on the keyboard. Glove 400 of FIG. 6G is another example of a monolithic electroactive polymer sensor where different active areas 404 of the monolithic polymer 402 each sense a different parameter change (motion of a finger). A sensor array similar to that shown in FIG. 5D could be located in a shoe to provide information on the pressure distribution across the foot.

The array may also comprise an array of sensors disposed at various locations in a physical system. This allows for detecting multiple parameters in a large structure or in disparate systems having many spatially separated points. In this case, a sensor array of the invention employs a plurality of individual electroactive polymer sensors at multiple locations, and each individual sensor detects a change in a parameter proximate to that location. One example of a disparate electroactive polymer sensor array is suit 420 of FIG. 6A. In one embodiment, each individual sensor is associated with a single electroactive polymer transducer. However, it should be borne in mind that it is also possible to associate more than one electroactive polymer sensor for each location or parameter, e.g. by using a monolithic transducer for multiple locations. Thus, multiple sensors implemented on a single large structure may not be identical and may record different events, properties, or have different structures and levels of complexity.

Each of the electroactive polymer portions, via their associated electrodes, in the sensor array are in electrical with communication sensing electronics designed or configured to detect the electrical changes from each electroactive polymer portion. Indeed, an advantage of electroactive polymer sensor arrays is that each electroactive polymer portion may provide independent measurement of the changing parameter (e.g., contact for each key on the keyboard may be separately detected).

In one application, a micro diaphragm sensor similar in structure to that described with respect to FIGS. 5D–E is implemented in an array on a single surface. By way of example, the array may include diaphragm portions 131 each with a diameter of 150 micrometers arranged in a planar configuration. The array may be formed on a silicon wafer. Micro diaphragm sensor arrays produced in this manner may include, for example, from 5 to 10,000 diaphragms each having a diameter in the range of 60 to 150 micrometers. The array may be placed upon perforated plates having suitably spaced holes for each diaphragm. Uses for these micro-sensor arrays include fluid flow sensors, haptic sensors, and high-spatial-resolution pressure sensors such as for artificial skins or force plates.

11. Conclusion

While this invention has been described in terms of several preferred embodiments, there are alterations, permutations, and equivalents that fall within the scope of this invention which have been omitted for brevity's sake. By way of example, although the present invention has been described in terms of several numerous applied material electrodes, the present invention is not limited to these materials and in some cases may include air as an electrode. In addition, although FIGS. 6C–F illustrate several fibrous electroactive polymer sensors suitable for use with the suit of FIG. 6A, other fibers such as flat fibers or ribbons may also be used. It is therefore intended that the scope of the invention should be determined with reference to the appended claims.

What is claimed is:

1. A sensor for detecting a change in a parameter, the sensor comprising:
    a transducer including at least two electrodes in electrical communication with an electroactive polymer wherein the electroactive polymer has an elastic modulus below about 100 MPa, the transducer configured such that a portion of the electroactive polymer deflects in response to the change in the parameter and the portion deflection produces an electrical change in the transducer; and
    sensing electronics in electrical communication with the at least two electrodes and designed or configured to detect the electrical change.

2. The sensor of claim 1 further comprising a logic device in electrical communication with the sensing electronics, the logic device configured to quantify the portion deflection using the electrical change received by the sensing electronics.

3. The sensor of claim 2 wherein the logic device is further configured to quantify the change in the parameter.

4. The sensor of claim 1 wherein the portion deflection produces an electrical impedance change in the transducer.

5. The sensor of claim 1 wherein the portion deflection produces a capacitance change in the transducer.

6. The sensor of claim 1 wherein the portion deflection produces a resistance change in the transducer.

7. The sensor of claim 1 further comprising a coupling mechanism that is a adapted for receiving input energy associated with the change in the parameter and transferring a portion of the input energy to the electroactive polymer.

8. The sensor of claim 7 wherein the coupling mechanism comprises a stiff member attached to the polymer and mechanically coupled to an object that produces the input energy associated with the change in the parameter.

9. The sensor of claim 7 wherein the coupling mechanism is a conductor in electrical communication with the transducer, the conductor providing electrical communication between the transducer and an object that produces a change in an electrical property.

10. The sensor of claim 9 wherein the portion deflection is produced as a result of a change in one of current, voltage, and resistance of the object.

11. The sensor of claim 1 wherein the transducer is configured to measure mechanical deflection of an object that the transducer is mechanically coupled to.

12. The sensor of claim 1 wherein the deflection of the portion of the electroactive polymer is a result of a change in at least one of strain, pressure, force, load, torque, displacement and temperature.

13. The sensor of claim 1 wherein the change in the parameter comprises a change in a physical property of the polymer.

14. The sensor of claim 13 wherein the change in the physical property of the polymer is the size of the polymer.

15. The sensor of claim 1 wherein the transducer is a monolithic transducer.

16. The sensor of claim 1 wherein the electroactive polymer is a dielectric elastomer.

17. The sensor of claim 1 wherein one or more of the at least two electrodes is compliant.

18. The sensor of claim 17 wherein the at least two electrodes comprise one of a colloidal suspension, a conductive grease, and a mixture of ionically conductive materials, a textured electrode, a high aspect ratio carbon material, and a conductive polymer.

19. The sensor of claim 1 further comprising a resistor that controls rate of charge moved to and from the polymer.

20. The sensor of claim 1 further comprising a voltage source in electrical communication with the at least two electrodes and configured to apply a voltage to the at least two electrodes.

21. The sensor of claim 1 wherein the sensing electronics communicate with the at least two electrodes using a wireless communication.

22. The sensor of claim 1 wherein the electroactive polymer is pre-strained.

23. A method of using an electroactive polymer transducer which comprises at least two electrodes in electrical communication with an electroactive polymer, the method comprising:
   applying a voltage difference between the at least two electrodes;
   deflecting the electroactive polymer wherein the electroactive polymer has an elastic modulus below about 100 MPa from a first position to a second position; and
   detecting an electrical change in the transducer resulting from the deflection from the first position to the second position.

24. The method of claim 23 further comprising quantitatively converting the electrical change to the deflection from the first position to the second position.

25. The method of claim 23 wherein an initial voltage applied between the at least two electrodes is less than the voltage required to actuate the electroactive polymer from the first position to the second position.

26. The method of claim 23 further comprising removing charge from the at least two electrodes during the deflection from the first position to the second position.

27. The method of claim 23 wherein the deflection from the first position to the second position is associated with a change in a parameter of an object that the transducer is coupled to.

28. The method of claim 27 further comprising quantitatively converting the electrical change to the change in the parameter.

29. The method of claim 27 wherein the parameter is a mechanical property of the object.

30. The method of claim 23 further comprising controlling rate of moving charge to and from the polymer.

31. The method of claim 23 wherein the voltage applied between the at least two electrodes is an AC voltage.

32. The method of claim 31 wherein the voltage applied between the at least two electrodes is between about 1 mV and about 10,000 V.

33. The method of claim 23 wherein detecting the electrical change comprises detecting one of a capacitance change and a resistance change in the transducer.

34. The method of claim 23 further including pre-straining the polymer before applying the voltage.

35. The method of claim 23 wherein the electroactive polymer is a dielectric elastomer.

36. The method of claim 23 wherein detecting the electrical change comprises transmitting the electrical change to sensing electronics in electrical communication with the at least two electrodes.

37. The method of claim 36 wherein the sensing electronics detect a resistance change in one of the at least two electrodes.

38. The method of claim 23 wherein the sensing a electronics detect a resistance change in the polymer resulting from the deflection.

39. The method of claim 38 wherein the sensing electronics detect a capacitance change in the polymer.

40. The method of claim 23 further comprising removing charge from the at least two electrodes during deflection from the first position to the second position.

41. A sensor for detecting a change in a parameter, the sensor comprising:
   a transducer including at least two electrodes in electrical communication with an electroactive polymer wherein the electroactive polymer has an elastic modulus below about 100 MPa, the transducer configured such that a portion of the electroactive polymer deflects in response to the change in the parameter and the portion deflection produces a capacitance change in the transducer, and
   sensing electronics in electrical communication with the at least two electrodes and designed or configured to detect the capacitance change.

42. The sensor of claim 41 wherein the capacitance change is produced in the electroactive polymer.

43. The sensor of claim 41 wherein the at least two electrodes have a resistance approximately less than about 10% of the electroactive polymer resistance.

44. The sensor of claim 41 further comprising a voltage source in electrical communication with the at least two electrodes and configured to apply a voltage to the at least two electrodes.

45. The sensor of claim 41 wherein the sensing electronics are configured to operate in an AC mode.

46. The sensor of claim 41 further comprising a logic device in electrical communication with the sensing electronics, the logic device configured to quantify the portion deflection using the electrical change received by the sensing electronics.

47. The sensor of claim 41 wherein the sensing electronics comprise a high resistance resistor in series with the at least two electrodes.

48. The sensor of claim 41 wherein one of the at least two electrodes is compliant.

49. A sensor for detecting a change in a parameter, the sensor comprising:
   a transducer including at least two electrodes in electrical communication with an electroactive polymer wherein the electroactive polymer has an elastic modulus below about 100 MPa, the transducer configured such that a portion of the electroactive polymer deflects in response to the change in the parameter and the portion deflection produces a resistance change in the transducer, and
   sensing electronics in electrical communication with the at least two electrodes and designed or configured to detect the resistance change.

50. The sensor of claim 49 wherein the portion deflection produces a resistance change in one of the at least two electrodes.

51. The sensor of claim 49 wherein the portion deflection produces a resistance change in the electroactive polymer resulting from the deflection.

52. The sensor of claim 51 wherein the at least two electrodes have a conductance greater than the electroactive polymer.

53. The sensor of claim 49 further comprising a voltage source in electrical communication with the at least two electrodes configured to apply a voltage to the at least two electrodes.

54. The sensor of claim 49 further comprising a resistor that controls rate of moving charge to and from the polymer.

55. The sensor of claim 54 wherein the resistor produces an RC time constant with the polymer that is at least faster than the rate of change of the parameter being measured.

56. The sensor of claim 49 wherein the sensing electronics detect a voltage change in response to the resistance change in the transducer.

57. The sensor of claim 56 further comprising a logic device in electrical communication with the sensing electronics, the logic device configured to quantify the portion deflection using the voltage change received by the sensing electronics.

58. The sensor of claim 56 wherein the sensing electronics operate in a DC mode.

59. The sensor of claim 49 wherein one of the at least two electrodes is compliant.

60. A sensor for detecting a change in a parameter, the sensor comprising:
a transducer including at least two electrodes in electrical communication with an electroactive polymer wherein the electroactive polymer has an elastic modulus below about 100 MPa, the transducer configured such that a portion of the electroactive polymer deflects in response to the change in the parameter and the portion deflection produces a resistance change in the electroactive polymer; and
sensing electronics in electrical communication with the at least two electrodes and designed or configured to detect the resistance change.

61. The sensor of claim 60 wherein the at least two electrodes have a conductance greater than the electroactive polymer.

62. The sensor of claim 60 wherein the sensing electronics communicate with the at least two electrodes using a wireless communication.

63. The sensor of claim 60 further comprising a voltage source in communication with the at least two electrodes and configured to apply a voltage to the at least two electrodes.

64. The sensor of claim 63 wherein the voltage source provides a high frequency AC signal.

65. The sensor of claim 60 further comprising a logic device in electrical communication with the sensing electronics, the logic device configured to quantify the portion deflection using the electrical change received by the sensing electronics.

66. The sensor of claim 60 wherein one of the at least two electrodes is compliant.

67. The sensor of claim 60 wherein the electroactive polymer is a dielectric elastomer.

68. The sensor of claim 60 further comprising a coupling mechanism that is designed or configured to receive input energy associated with the change in the parameter and transfer a portion of the input energy to the electroactive polymer.

69. A sensor for detecting a change in a parameter, the sensor comprising:
a transducer including at least two electrodes in electrical communication with an electroactive polymer wherein the electroactive polymer has an elastic modulus below about 100 MPa, the transducer configured such that a portion of the electroactive polymer deflects in response to the change in the parameter and the portion deflection produces a resistance change in one of the at least two electrodes; and
sensing electronics in electrical communication with the at least two electrodes and designed or configured to detect the resistance change.

70. The sensor of claim 69 wherein the one of at least two electrodes comprise carbon fibrils.

71. The sensor of claim 70 wherein the at least two electrodes comprise one of a colloidal suspension, a conductive grease, a mixture of ionically conductive materials, a textured electrode, a high aspect ratio carbon material, and a conductive polymer.

72. The sensor of claim 69 further comprising a voltage source in communication with the at least two electrodes configured to apply a voltage to the at least two electrodes.

73. The sensor of claim 72 wherein the voltage source provides a high frequency AC signal.

74. The sensor of claim 69 wherein one of the at least two electrodes is compliant.

75. A sensor for detecting a change in a parameter, the sensor comprising:
a transducer including at least two electrodes in electrical communication with an electroactive polymer wherein the electroactive polymer has an elastic modulus below about 100 MPa, the transducer configured such that a portion of the electroactive polymer deflects in response to the change in the parameter and the portion deflection produces an impedance change in the transducer; and
sensing electronics in electrical communication with the at least two electrodes and designed or configured to detect the impedance change.

76. The sensor of claim 75 wherein the impedance change comprises a resistance change in the electroactive polymer.

77. The sensor of claim 75 wherein the impedance change comprises a resistance change in one of the at least two electrodes.

78. The sensor of claim 75 wherein the impedance change comprises a capacitance change in the electroactive polymer.

79. The sensor of claim 75 further comprising a voltage source in electrical communication with the at least two electrodes configured to apply a voltage to the at least two electrodes.

80. The sensor of claim 75 wherein the sensing electronics detect a voltage change in response to the resistance change in the transducer.

81. The sensor of claim 75 wherein the electroactive polymer is a dielectric elastomer.

82. The sensor of claim 75 wherein one of the at least two electrodes is compliant.

83. A sensor array for detecting a change in one or more parameters, the sensor array comprising:
at least one transducer comprising, at least two electrodes coupled to a first portion of at least one electroactive polymer wherein first portion the one electroactive polymer has an elastic modulus below about 100 MPa, the at least one transducer configured such that the first portion deflects in response to a first change in the one or more parameters and the first portion deflection produces a first electrical change in the at least one transducer;
at least two electrodes coupled to a second portion of the at least one electroactive polymer, the at least one transducer configured such that the second portion deflects in response to a second change in the one or more parameters and the second portion deflection produces a second electrical change in the at least one transducer; and
sensing electronics in electrical communication with the at least two electrodes coupled to the first portion and in electrical communication with the at least two electrodes coupled to the second portion, the sensing electronics designed or configured to detect the first and second electrical change.

84. The sensor array of claim 83 wherein the at least one electroactive polymer is a monolithic electroactive polymer and the first portion and the second portion are both portions of the monolithic polymer.

85. The sensor array of claim 83 wherein the first portion of the at least one electroactive polymer responds to the first change independently to response of the second portion to the second change.

86. The sensor array of claim 83 further comprising a logic device in electrical communication with the sensing electronics, the logic device configured to quantify the first and second change using the electrical change received by the sensing electronics.

87. The sensor array of claim 83 further comprising a coupling mechanism that is designed to configured to receive adapted for receiving input energy associated with the first change in the one or more parameters and for transferring a portion of the input energy to the at least one electroactive polymer.

88. The sensor array of claim 83 wherein the at least one transducer is configured to measure mechanical deflection of an object that the transducer is mechanically coupled to.

89. The sensor array of claim 83 wherein the array comprises two transducers, and the first portion is included in a first electroactive polymer of the first transducer and the second portion is included in a second electroactive polymer of the second transducer.

90. The sensor array of claim 83 wherein the sensing electronics are configured to provide electrical energy to the at least two electrodes coupled to the first portion without providing electrical energy to the at least two electrodes coupled to the second portion.

91. The sensor array of claim 83 wherein the portion deflection produces a capacitance change in the transducer.

92. A sensor for detecting a change in a parameter, the sensor comprising:
a transducer including at least two electrodes in electrical communication with an electroactive polymer, the transducer configured such that a portion of the electromotive polymer deflects in response to the change in the parameter and the portion deflection produces an electrical change in the transducer;
sensing electronics in electrical communication with the at least two electrodes and designed or configured to detect the electrical change;
a coupling mechanism adapted for receiving input energy associated with the change in the parameter and for transferring a portion of the input energy to the electroactive polymer wherein the coupling mechanism is a conductor in electrical communication with the transducer, the conductor providing electrical communication between the transducer and an object that produces a change in an electrical property.

93. A method of using an electroactive polymer transducer which comprises at least two electrodes in electrical communication with an electroactive polymer, the method comprising:
applying a voltage difference between the at least two electrodes;
deflecting the electroactive polymer from a first position to a second position; and
detecting an electrical change in the transducer resulting from the deflection from the first position to the second position wherein the deflection from the first position to the second position is associated with a change in a parameter of an object that the transducer is coupled to.

94. A sensor for detecting a change in a parameter, the sensor comprising:
a transducer including at least two electrodes in electrical communication with an electroactive polymer wherein the at least two electrodes have a resistance approximately less than about 10% of the electroactive polymer resistance, the transducer configured such that a portion of the electroactive polymer deflects in response to the change in the parameter and the portion deflection produces a capacitance change in the transducer; and
sensing electronics in electrical communication with the at least two electrodes and designed or configured to detect the capacitance change.

95. A sensor for detecting a change in a parameter, the sensor comprising:
a transducer including at least two electrodes in electrical communication with an electroactive polymer, the transducer configured such that a portion of the electroactive polymer deflects in response to the change in the parameter and the portion deflection produces at least one of i) a capacitance change in the transducer, ii) a resistance change in the transducer; iii) an impedance change in the transducer or iv) combinations thereof;
sensing electronics in electrical communication with the at least two electrodes and designed or configured to detect at least one of the capacitance change, the resistance change; the impedance change or combinations thereof and
a voltage source in electrical communication with the at least two electrodes and configured to apply a voltage to the at least two electrodes.

96. The sensor of claim 95, wherein the resistance change of the transducer comprises a resistance change in one of the electroactive polymer, one or more of the at least two electrodes or combinations thereof.

97. A sensor array for detecting a change in one or more parameters, the sensor array comprising:
at least one transducer comprising,
at least two electrodes coupled to a first portion of at least one electroactive polymer, the at least one transducer configured such that the first portion deflects in response to a first change in the one or more parameters and the first portion deflection produces a first electrical change in the at least one transducer;
at least two electrodes coupled to a second portion of the at least one electroactive polymer, the at least one transducer configured such that the second portion deflects in response to a second change in the one or more parameters and the second portion deflection produces a second electrical change in the at least one transducer;
sensing electronics in electrical communication with the at least two electrodes coupled to the first portion and in electrical communication with the at least two electrodes coupled to the second portion, the sensing electronics designed or configured to detect the first and second electrical change; and
a logic device in electrical communication with the sensing electronics, the logic device configured to quantify the first and second change using the electrical change received by the sensing electronics.

98. A sensor array for detecting a change in one or more parameters, the sensor array comprising:
at least one transducer comprising,
at least two electrodes coupled to a first portion of at least one electroactive polymer, the at least one transducer configured such that the first portion deflects in response to a first change in the one or more parameters and the first portion deflection produces a first electrical change in the at least one transducer;

at least two electrodes coupled to a second portion of the at least one electroactive polymer, the at least one transducer configured such that the second portion deflects in response to a second change in the one or more parameters and the second portion deflection produces a second electrical change in the at least one transducer; and sensing electronics in electrical communication with the at least two electrodes coupled to the first portion and in electrical communication with the at least two electrodes coupled to the second portion, the sensing electronics designed or configured to detect the first and second electrical change wherein the array comprises two transducers, and the first portion is included in a first electroactive polymer of the first transducer and the second portion is included in a second electroactive polymer of the second transducer.

99. A sensor for detecting a change in a parameter, the sensor comprising:

a transducer including at least two electrodes in electrical communication with an electroactive polymer, the transducer configured such that a portion of the electroactive polymer deflects in response to the change in the parameter and the portion deflection produces an electrical change in the transducer wherein the electroactive polymer is pre-strained; and sensing electronics in electrical communication with the at least two electrodes and designed or configured to detect the electrical change.

100. The sensor of claim 1 wherein one of a linear strain or an area strain is generated in the electroactive polymer by the deflection of the portion of the electroactive polymer.

101. The sensor of claim 100, wherein the strain is greater than about 1%.

102. The sensor of claim 100, wherein the strain is greater than about 10%.

103. The sensor of claim 1, wherein the sensor is integrated into or coupled to an object.

104. The sensor of claim 103, wherein the sensor is integrated into the object and is an inherent part of a structure of the object.

105. The sensor of claim 103, wherein the sensor is conformal to a surface of the object.

106. The sensor of claim 103, wherein the object is a textile or a fabric.

107. The sensor of claim 103, wherein the object is worn by a person.

108. The sensor of claim 103, wherein the object is a belt, glove or a piece of clothing.

109. The sensor of claim 103, wherein the object is a seat for a person.

110. The sensor of claim 109 wherein the sensor is adapted for detecting when a person is sitting in the seat.

111. The sensor of claim 109, wherein the seat is located in an automobile.

112. The sensor of claim 103, wherein the object is a medical device.

113. The sensor of claim 103, wherein the object is one of a toy, a doll, an animated device or a robotic device.

114. The sensor of claim 113, wherein the change in the parameter detected by the sensor is for triggering an action in the toy, the doll, the animated device or the robotic device.

115. The sensor of claim 1, wherein the sensor is adapted for measuring a biological property of a biological substance or a biological tissue.

116. The sensor of claim 115, wherein the biological substance or the biological tissue is one of bone, muscle, skin, a blood vessel, an organ or combinations thereof.

117. The sensor of claim 1, wherein the sensor is adapted for providing haptic feedback.

\* \* \* \* \*